US011701390B2

(12) United States Patent
Bigger et al.

(10) Patent No.: US 11,701,390 B2
(45) Date of Patent: Jul. 18, 2023

(54) GENE THERAPY

(71) Applicant: The University of Manchester, Manchester (GB)

(72) Inventors: Brian Bigger, Manchester (GB); Hélène Gleitz, Rotterdam (NL)

(73) Assignee: The University of Manchester, Manchester (GB)

( * ) Notice: Subject to any disclaimer, the term of this patent is extended or adjusted under 35 U.S.C. 154(b) by 456 days.

(21) Appl. No.: 16/484,311

(22) PCT Filed: Feb. 7, 2018

(86) PCT No.: PCT/GB2018/050347
§ 371 (c)(1),
(2) Date: Aug. 7, 2019

(87) PCT Pub. No.: WO2018/146473
PCT Pub. Date: Aug. 16, 2018

(65) Prior Publication Data
US 2020/0000854 A1    Jan. 2, 2020

(30) Foreign Application Priority Data

Feb. 7, 2017 (GB) .................................... 1701968

(51) Int. Cl.
| | |
|---|---|
| *C12N 15/63* | (2006.01) |
| *C07H 21/04* | (2006.01) |
| *A61K 35/28* | (2015.01) |
| *C07K 14/775* | (2006.01) |
| *C12N 5/16* | (2006.01) |
| C12N 15/79 | (2006.01) |

(52) U.S. Cl.
CPC ............ *A61K 35/28* (2013.01); *C07K 14/775* (2013.01); *C12N 5/16* (2013.01); *C12N 15/63* (2013.01); *C07H 21/04* (2013.01); *C12N 15/79* (2013.01); *C12N 2510/00* (2013.01)

(58) Field of Classification Search
CPC .... C12N 15/79; C12N 15/85; C12N 2510/00; C12N 15/63; C07H 21/04
See application file for complete search history.

(56) References Cited

FOREIGN PATENT DOCUMENTS

| WO | WO 2004/108071 A2 | 12/2004 |
| WO | WO 2012/159052 A2 | 11/2012 |
| WO | WO 2013/078562 A2 | 6/2013 |
| WO | WO 2016/077356 A2 * | 5/2016 |

OTHER PUBLICATIONS

Diamond et al., 2014, US 20140186401 A1, effective filing date Apr. 28, 2011.*
Sugimura et al., 2011, GeneSeq Accession No. AZM63958, computer printout, pp. 1-3.*
Scadden et al., 2008, US 20080057579 A1.*
Aldenhoven et al., "Hematopoietic cell transplantation for mucopolysaccharidosis patients is safe and effective: results after implementation of international guidelines," Biology of blood and marrow transplantation: journal of the American Society for Blood and Marrow Transplantation, vol. 21(6), pp. 1106-1109 (2015a).
Aldenhoven et al., "Long-term outcome of Hurler syndrome patients after hematopoietic cell transplantation: an international multicenter study," Blood, vol. 125(13), pp. 2164-2172 (2015b).
Baehner et al., "Cumulative incidence rates of the mucopolysaccharidoses in Germany," Journal of inherited metabolic disease, vol. 28(6), pp. 1011-1017 (2005).
Biffi et al., "Correction of metachromatic leukodystrophy in the mouse model by transplantation of genetically modified hematopoietic stem cells," The Journal of clinical investigation, vol. 113(8), pp. 1118-1129 (2004).
Biffi et al., "Hematopoietic Stem Cell Gene Therapy for Lysosomal Storage Disorders: Expected Benefits and Limitations," Stem Cells Biol Reg, pp. 127-138 (2013).
Bigger et al., "Permanent partial phenotypic correction and tolerance in a mouse model of hemophilia B by stem cell gene delivery of human factor IX," Gene therapy, vol. 13(2), pp. 117-126 (2005).
Bockenhoff et al., "Comparison of Five Peptide Vectors for Improved Brain Delivery of the Lysosomal Enzyme Arylsulfatase A," The Journal of Neuroscience, vol. 34(9), pp. 3122-3129 (2014).
International Preliminary Report on Patentability and Written Opinion of the International Searching Authority corresponding to International Application No. PCT/GB2018/050347 dated Aug. 22, 2019.
International Search Report corresponding to International application No. PCT/GB2018/050347 dated Apr. 18, 2018.
Great Britain Search Report corresponding to Patent Application No. GB 1701968.8 dated Dec. 11, 2017.
Boelens et al., "Outcomes of transplantation using various hematopoietic cell sources in children with Hurler syndrome after myeloablative conditioning," Blood, vol. 121(19), pp. 3981-3987 (2013).

(Continued)

*Primary Examiner* — Shin Lin Chen
(74) *Attorney, Agent, or Firm* — Jenkins, Wilson, Taylor & Hunt, P.A.

(57) ABSTRACT

The present invention relates generally to polypeptides or nucleic acids for use in the treatment, management, retardation of progression or normalisation of development of an iduronate-2-sulfatase (IDS) deficiency and/or Mucopolysaccharidosis type II (MPS II) in an individual, wherein the polypeptides comprise iduronate-2-sulfatase (IDS) tethered to a tandem repeat of Apolipoprotein E (ApoEII) or the nucleic acids comprise an iduronate-2-sulfatase (IDS) gene sequence tethered to a tandem repeat of the Apolipoprotein E (ApoEII) gene sequence. The invention also relates to haematopoietic stem and progenitor cells (HSPCs) transduced by such nucleic acids for use in therapies.

7 Claims, 17 Drawing Sheets

Figure 1:
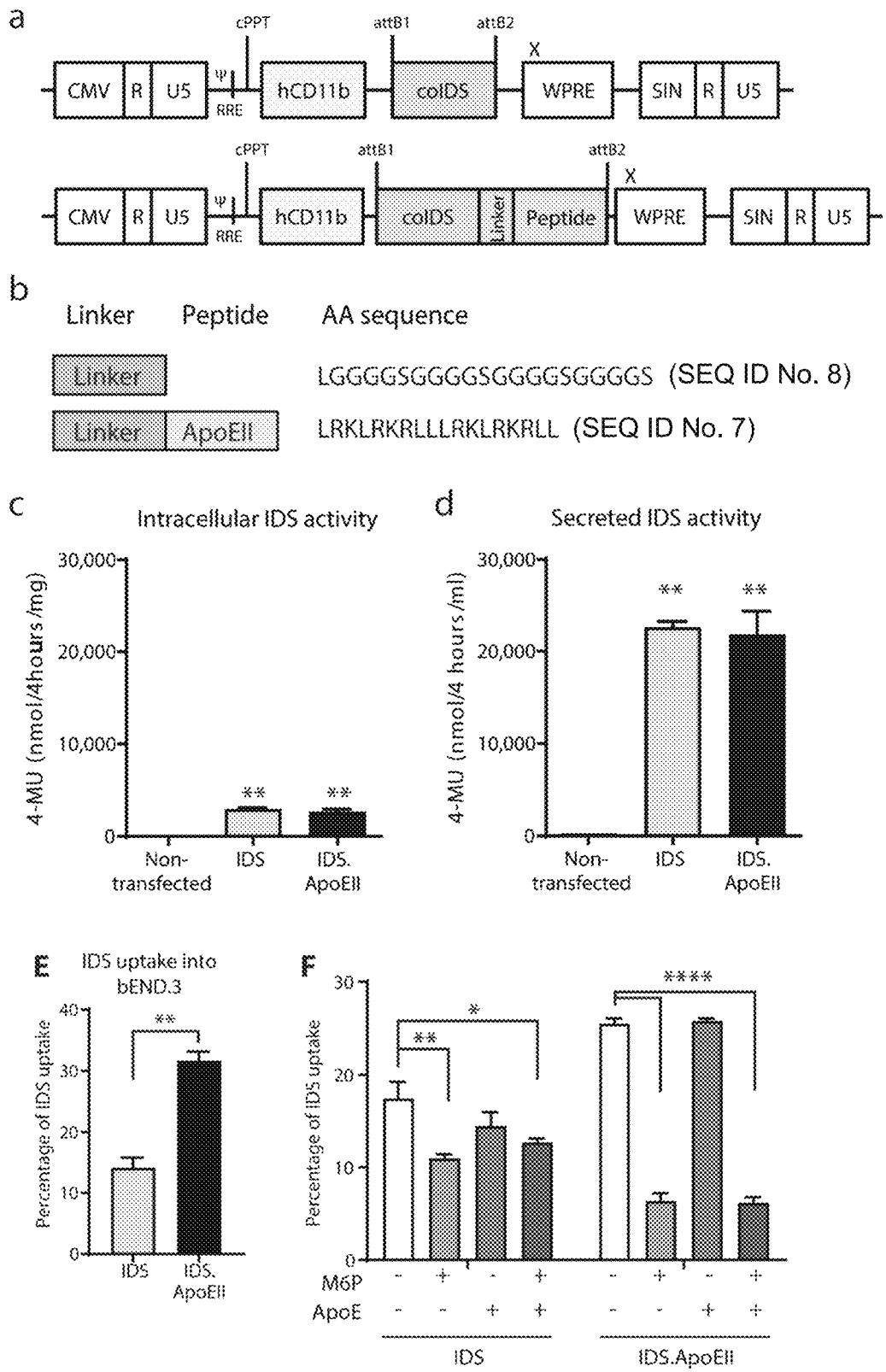

Specification includes a Sequence Listing.

(56) References Cited

OTHER PUBLICATIONS

Boren et al., "Identification of the low density lipoprotein receptor-binding site in apolipoprotein B100 and the modulation of its binding activity by the carboxyl terminus in familial defective apo-B100," The Journal of clinical investigation, vol. 101(5), pp. 1084-1093 (1998).
Brooks et al., "Significance of immune response to enzyme-replacement therapy for patients with a lysosomal storage disorder," Trends in Molecular Medicine, vol. 9(10), pp. 450-453 (2003).
Cardone et al., "Correction of Hunter syndrome in the MPSII mouse model by AAV2/8-mediated gene delivery," Human Molecular Genetics, vol. 15(7), pp. 1225-1236 (2006).
El-Amouri et al., "Normalization and Improvement of CNS Deficits in Mice With Hurler Syndrome After Long-term Peripheral Delivery of BBB-targeted Iduronidase," Molecular Therapy: The Journal of the American Society of Gene Therapy, vol. 22(12), pp. 2028-2037 (2014).
Eng et al., "Clinical benefit of enzyme replacement therapy (ERT) in mucopolysaccharidosis II (MPS II, Hunter syndrome)," Molecular Genetics and Metabolism, vol. 92(4), Article ID S18-S (2007).
Guffon et al., "Bone marrow transplantation in children with Hunter syndrome: outcome after 7 to 17 years," The Journal of pediatrics, vol. 154(5), pp. 733-737 (2009).
Hinderer et al., "Delivery of an adeno-associated virus vector into Cerebrospinal Fluid attenuates central nervous system disease in mucopolysaccharidosis type II mice," Hum Gene Ther, vol. 27, No. 11, pp. 906-915 (2016).
Holley et al., "Mucopolysaccharidosis Type I, Unique Structure of Accumulated Heparan Sulfate and Increased N-Sulfotransferase Activity in Mice Lacking alpha-L-iduronidase," Journal of Biological Chemistry, vol. 286(43), pp. 37515-37524 (2011).
Holt et al., "Natural Progression of Neurological Disease in Mucopolysaccharidosis Type II," Pediatrics, vol. 127(5), pp. E1258-1265 (2011).
Kuroda et al., "Simplified lentivirus vector production in protein-free media using polyethylenimine-mediated transfection," J Virol Method, vol. 157(2), pp. 113-121 (2009).
Langford-Smith et al., "Hematopoietic stem cell and gene therapy corrects primary neuropathology and behavior in mucopolysaccharidosis IIIA mice," Molecular therapy: the journal of the American Society of Gene Therapy. Vol. 20(8), pp. 1610-1621 (2012).
Lu et al., "Genetic engineering of a bifunctional IgG fusion protein with iduronate-2-sulfatase," Bioconjugate chemistry, vol. 21(1), pp. 151-156 (2010).
Meikle et al., "Prevalence of lysosomal storage disorders," Jama, vol. 281(3), pp. 249-254 (1999).
Motas et al., "CNS-directed gene therapy for the treatment of neurologic and somatic mucopolysaccharidosis type II (Hunter syndrome)," JCI Insight, vol. 1(9), pp. 1-18 (2016).
Muenzer et al., "A phase II/III clinical study of enzyme replacement therapy with idursulfase in mucopolysaccharidosis II (Hunter syndrome)," Genetics in Medicine, vol. 8(8), pp. 465-473 (2006).
Muenzer et al., "Long-term, open-labeled extension study of idursulfase in the treatment of Hunter syndrome," Genetics in Medicine, vol. 13(2), pp. 95-101 (2011).
Nolan et al., "Quantification of mRNA using real-time RT-PCR," Nature protocols, vol. 1(3), pp. 1559-1582 (2006).

O'Tuathaigh et al., "Phenotypic characterization of spatial cognition and social behavior in mice with 'knockout' of the schizophrenia risk gene neuregulin 1," Neuroscience, vol. 147(1), pp. 18-27 (2007).
Oller-Salvia et al., "Blood-brain barrier shuttle peptides: an emerging paradigm for brain delivery," Chem. Soc. Rev., vol. 45, pp. 4690-4707 (2016).
Pardridge, "Molecular biology of the blood-brain barrier," Molecular biotechnology, vol. 30(1), pp. 57-69 (2005).
Pardridge, "Targeting neurotherapeutic agents through the blood-brain barrier," Archives of neurology, vol. 59(1), pp. 35-40 (2002).
Poorthuis et al., "The frequency of lysosomal storage diseases in The Netherlands," Human genetics, vol. 105, pp. 151-156 (1999).
Scarpa et al., "Mucopolysaccharidosis type II: European recommendations for the diagnosis and multidisciplinary management of a rare disease," Orphanet journal of rare diseases, vol. 6, Article No. 72, pp. 1-18 (2011).
Sergijenko et al., "Myeloid/Microglial driven autologous hematopoietic stem cell gene therapy corrects a neuronopathic lysosomal disease," Molecular therapy: the journal of the American Society of Gene Therapy, vol. 21(10), pp. 1938-1949 (2013).
Siapati et al., "Comparison of HIV- and EIAV-based vectors on their efficiency in transducing murine and human hematopoietic repopulating cells," Molecular Therapy, vol. 12(3), pp. 537-546 (2005).
Sorrentino et al., "A highly secreted sulphamidase engineered to cross the blood-brain barrier corrects brain lesions of mice with mucopolysaccharidoses type IIIA," Embo Nol Med, vol. 5(5), pp. 675-690 (2013).
Spencer et al., "A neuroprotective brain-penetrating endopeptidase fusion protein ameliorates Alzheimer disease pathology and restores neurogenesis," The journal of biological chemistry, vol. 289(25), pp. 17917-17931 (2014).
Spencer et al., "Targeted delivery of proteins across the blood-brain barrier," Proc Natl Acad Sci U.S.A., vol. 104(18), pp. 7594-7599 (2007).
Vellodi et al., "Long-term follow-up following bone marrow transplantation for Hunter disease," Journal of inherited metabolic disease, vol. 22, pp. 638-648 (1999).
Visigalli et al., "Gene therapy augments the efficacy of hematopoietic cell transplantation and fully corrects mucopolysaccharidosis type I phenotype in the mouse model," Blood, vol. 116(24), pp. 5130-5139 (2010).
Wakabayashi et al., "Hematopoietic Stem Cell Gene Therapy Corrects Neuropathic Phenotype in Murine Model of Mucopolysaccharidosis Type II," Hum Gene Ther, vol. 26, pp. 357-366 (2015).
Wang et al., "Engineering a lysosomal enzyme with a derivative of receptor-binding domain of apoE enables delivery across the blood-brain barrier," Proceedings National Academy of Sciences PNAS, vol. 110(8), pp. 2999-3004 (2013).
Wilkinson et al., "Neuropathology in mouse models of mucopolysaccharidosis type I, IIIA and IIIB," PloS one, vol. 7(4), Article ID e35787 (2012).
Wraith et al., "Mucopolysaccharidosis type II (Hunter syndrome): a clinical review and recommendations for treatment in the era of enzyme replacement therapy," European Journal of Pediatrics, vol. 167(3), pp. 267-277 (2008).
Jiang et al., "Motor and behavioral phenotype in conditional mutants with targeted ablation of cortical D1 dopamine receptor-expressing cells," Neurobiology of disease, vol. 76, pp. 137-158 (2015).
Neufeld et al., "The Mucopolysaccharidoses," Lysomal Disorders, pp. 3421-3452 McGraw-Hill, 2001.
Sambrook et al. "Molecular Cloning: A laboratory manual," Review in Biochemical Education 11(2), 1 page (1983).

* cited by examiner

Figure 2:
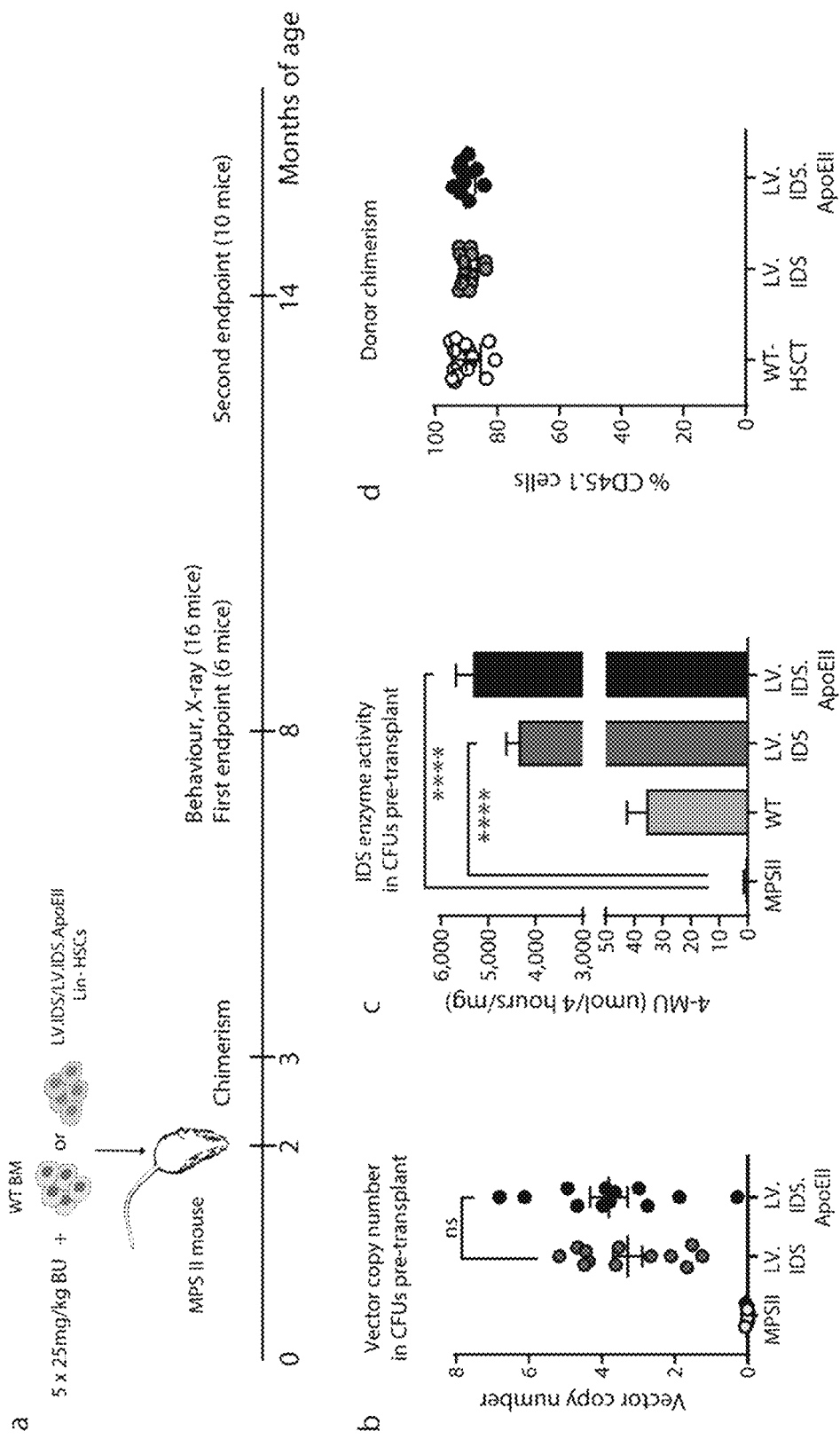
Figure 2:
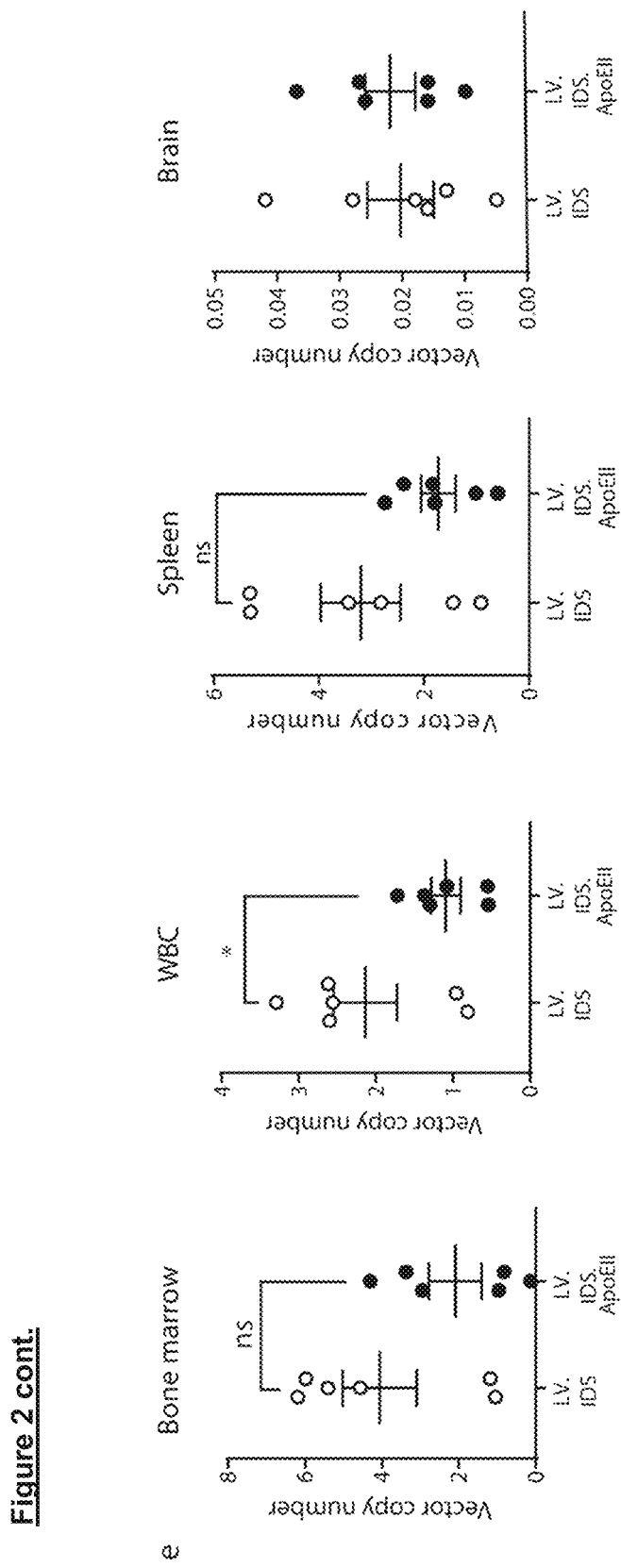
Figure 2:
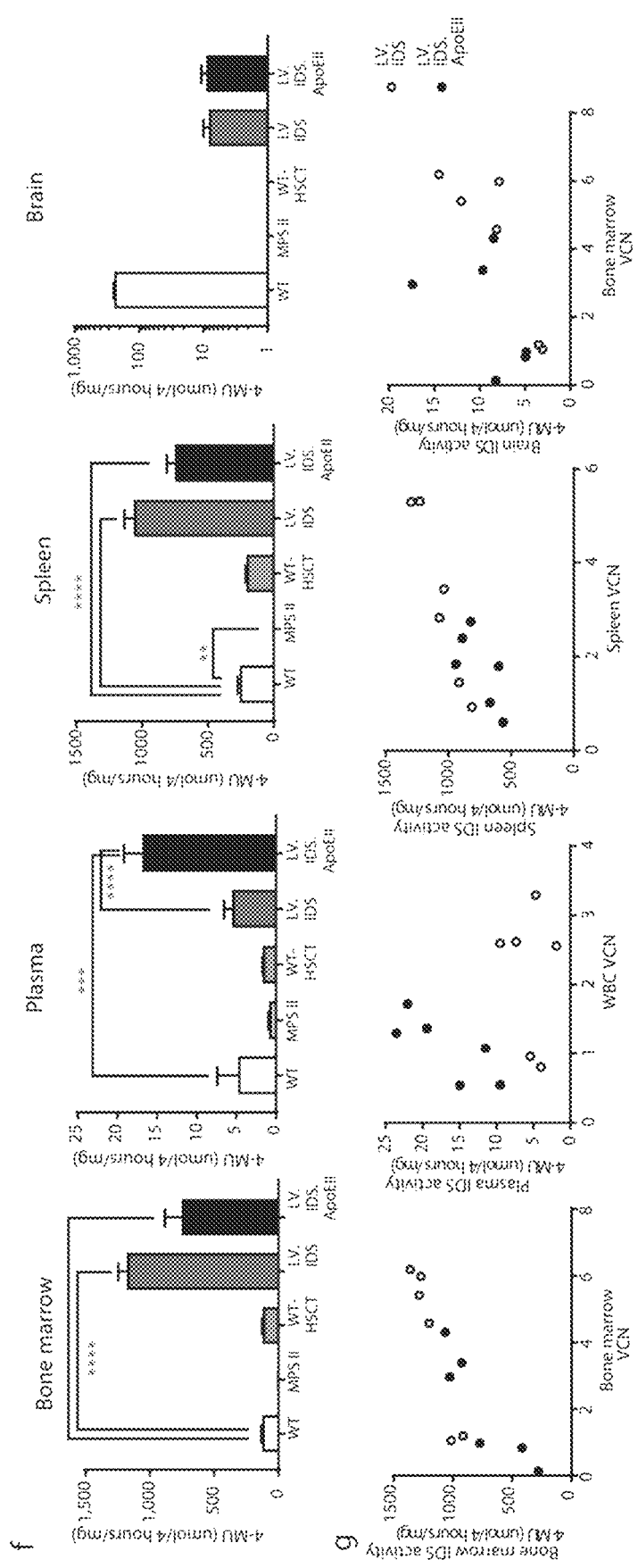

Figure 2 cont.
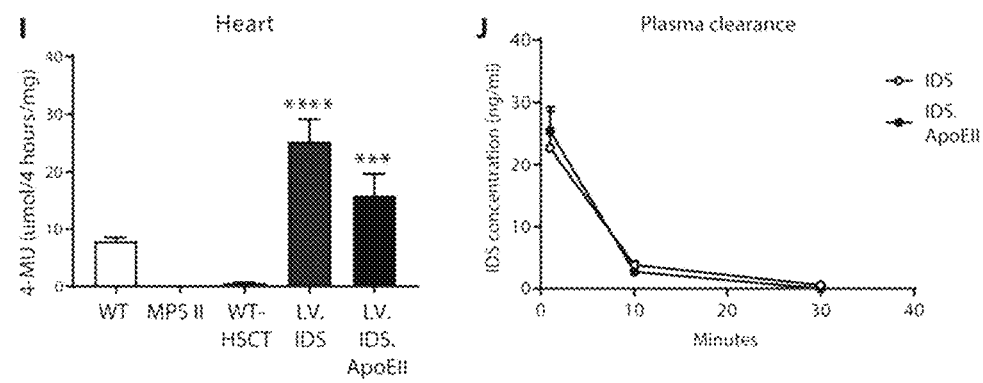
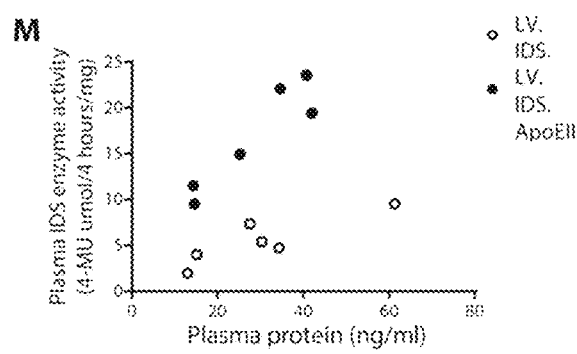
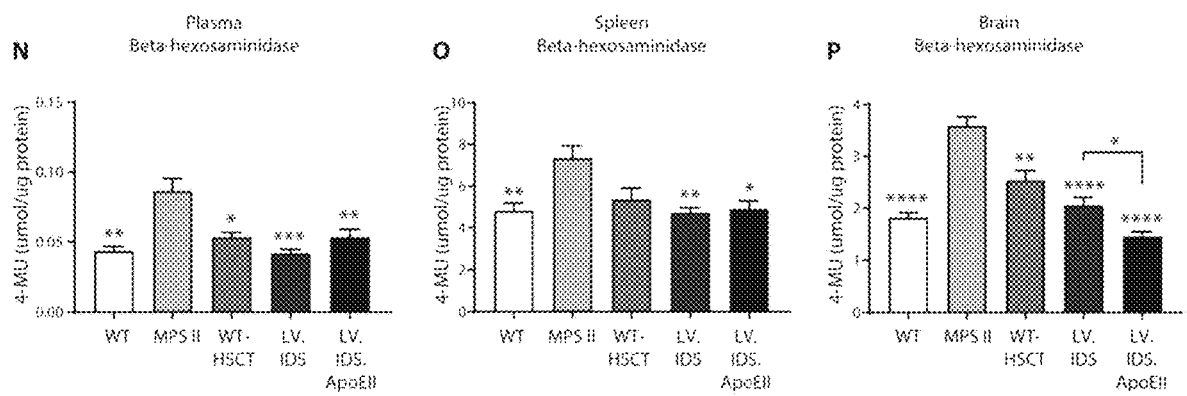

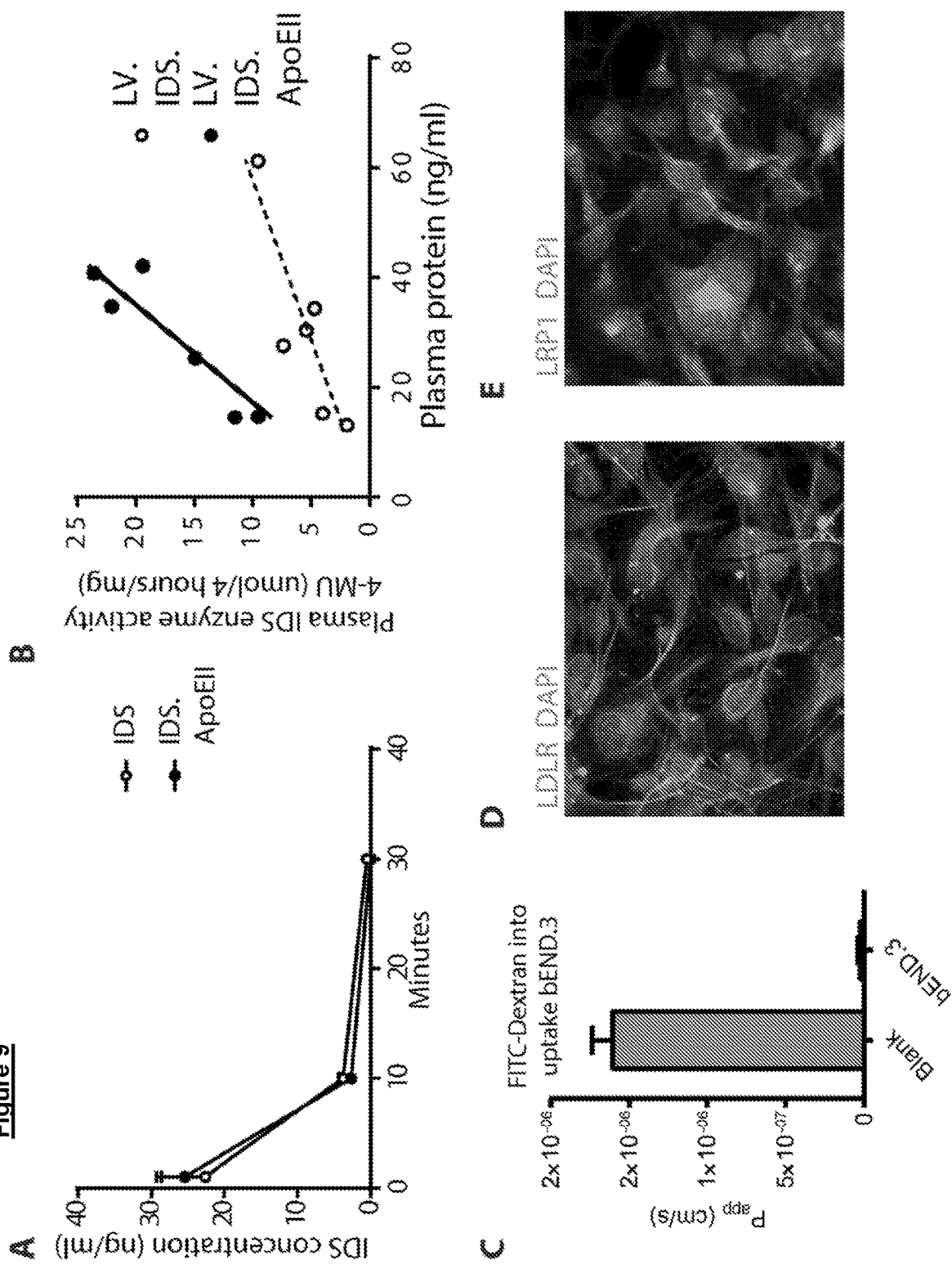

SEQUENCE LISTING

```
<160> NUMBER OF SEQ ID NOS: 8

<210> SEQ ID NO 1
<211> LENGTH: 1650
<212> TYPE: DNA
<213> ORGANISM: Artificial Sequence
<220> FEATURE:
<223> OTHER INFORMATION: coIDS DNA sequence

<400> SEQUENCE: 1
atgcctccac ctagaactgg aagaggcctg ctgtggctgg gcctggtgct gtctagtgtg      60
tgtgtggccc tgggcagcga gacacaggcc aacagcacaa ccgacgccct gaacgtgctg     120
ctgatcatcg tggacgacct gaggcctagc ctgggctgct acggcgataa gctcgtgcgg     180
agccccaaca tcgatcagct ggcctctcac agcctgctgt tccagaacgc attcgcacag     240
caggcagtgt gcgcccccag cagagtgtct ttcctgaccg gcagaaggcc cgacaccacc     300
cggctgtacg acttcaacag ctactggcgg gtgcacgccg gcaacttcag caccatcccc     360
cagtacttca agaaaacgg ctacgtgacc atgagcgtgg gcaaggtgtt ccaccccggc     420
atcagctcca accacaccga cgacagcccc tacagctggt ccttcccacc ctaccaccc     480 agcagcgaga agtacgagaa caccaagacc tgcagaggcc ccgacggcga gctgcatgcc     540
aatctgctgt gccccgtgga cgtgctggat gtgcctgagg aaccctgcc cgacaagcag     600 tctaccgagc aggccattca gctgctggaa aagatgaaga ccagcgccag ccccttcttc     660
ctggccgtgg gctatcacaa gccccacatc cctttcagat accccaaaga gttccagaag     720
ctgtaccccc tggaaaacat caccctggcc ccgatcctga ggtgccaga tggactgcct     780
```

| | |
|---|---|
| cccgtggcct acaacccctg gatggacatc cggcagcgcg aggatgtgca ggccctgaat | 840 |
| atcagcgtgc cctacggccc catcccccgtg gatttccagc ggaagatccg gcagagctac | 900 |
| ttcgccagcg tgtcctacct ggacacccaa gtgggcagac tgctgagcgc cctggacgat | 960 |
| ctgcagctgg ccaactccac catcattgcc ttcaccagcg accacggctg ggccctggga | 1020 |
| gaacatggcg agtgggccaa gtacagcaac ttcgacgtgg ccacccacgt gcccctgatc | 1080 |
| ttctacgtgc caggcagaac cgccagcctg cctgaggctg cgagaagct gttcccttac | 1140 |
| ctggacccct cgacagcgc ctcccagctg atggaacctg gcagacagag catggacctg | 1200 |
| gtggaactgg tgtccctgtt ccccacactg gccggactgg ctggactgca ggtgcccccct | 1260 |
| agatgtcccg tgcctagctt tcacgtggaa ctgtgcagag agggcaagaa cctgctgaag | 1320 |
| cacttccggt tccgggacct ggaagaagat ccctacctgc ccgcaaccc cagagagctg | 1380 |
| atcgcctaca gccagtaccc cagacccagc gacatccctc agtggaacag cgacaagccc | 1440 |
| agcctgaagg acatcaagat catgggctac agcatccgga ccatcgacta ccggtacacc | 1500 |
| gtgtgggtgg gattcaaccc cgacgagttc ctggccaatt tctccgacat ccacgccggg | 1560 |
| gagctgtact cgtggacag cgatcccctg caggaccaca acatgtacaa cgacagccag | 1620 |
| ggcggcgacc tgttccagct gctgatgccc | 1650 |

<210> SEQ ID NO 2
<211> LENGTH: 1650
<212> TYPE: DNA
<213> ORGANISM: Homo sapiens

<400> SEQUENCE: 2

| | |
|---|---|
| atgccgccac cccggaccgg ccgaggcctt ctctggctgg gtctggttct gagctccgtc | 60 |
| tgcgtcgccc tcgatccga aacgcaggcc aactcgacca cagatgctct gaacgttctt | 120 |
| ctcatcatcg tggatgacct gcgcccctcc ctgggctgtt atggggataa gctggtgagg | 180 |
| tccccaaata ttgaccaact ggcatcccac agcctcctct tccagaatgc ctttgcgcag | 240 |
| caagcagtgt gcgccccgag ccgcgtttct ttcctcactg gcaggagacc tgacaccacc | 300 |
| cgcctgtacg acttcaactc ctactggagg gtgcacgctg aaacttctc caccatcccc | 360 |
| cagtacttca aggagaatgg ctatgtgacc atgtcggtgg aaaagtcttt caccctgggg | 420 |
| atatcttcta accataccga tgattctccg tatagctggt cttttccacc ttatcatcct | 480 |
| tcctctgaga agtatgaaaa cactaagaca tgtcgagggc cagatggaga actccatgcc | 540 |
| aacctgcttt gccctgtgga tgtgctggat gttcccgagg gcaccttgcc tgacaaacag | 600 |
| agcactgagc aagccataca gttgttggaa aagatgaaaa cgtcagccag tcctttcttc | 660 |
| ctggccgttg gtatcataa gccacacatc cccttcagat accccaagga atttcagaag | 720 |
| ttgtatcctc tggagaacat caccctggcc cccgatcccg aggtccctga tggcctaccc | 780 |
| cctgtggcct acaaccctg gatggacatc aggcaacggg aagacgtcca agccttaaac | 840 |
| atcagtgtgc cgtatggtcc aattcctgtg gactttcagc ggaaaatccg ccagagctac | 900 |
| tttgcctctg tgtcatattt ggatacacag gtcggccgcc tcttgagtgc tttggacgat | 960 |
| cttcagctgg ccaacagcac catcattgca tttacctcgg atcatgggtg ggctctaggt | 1020 |
| gaacatggag aatgggccaa atacagcaat tttgatgttg ctacccatgt tccctgata | 1080 |
| ttctatgttc ctggaaggac ggcttcactt ccggaggcag gcgagaagct ttcccttac | 1140 |
| ctcgacccct tgattccgc ctcacagttg atggagccag gcaggcaatc catgaccttg | 1200 |
| gtggaacttg tgtctctttt tcccacgctg gctggacttg caggactgca ggttccacct | 1260 |

```
cgctgccccg ttccttcatt tcacgttgag ctgtgcagag aaggcaagaa ccttctgaag    1320 catttcgat tccgtgactt ggaagaggat ccgtacctcc ctggtaatcc ccgtgaactg    1380
attgcctata gccagtatcc ccggccttca gacatccctc agtggaattc tgacaagccg    1440
agtttaaaag atataaagat catgggctat tccatacgca ccatagacta taggtatact    1500
gtgtgggttg gcttcaatcc tgatgaattt ctagctaact tttctgacat ccatgcaggg    1560
gaactgtatt ttgtggattc tgacccattg caggatcaca atatgtataa tgattcccaa    1620
ggtggagatc ttttccagtt gttgatgcct                                     1650

<210> SEQ ID NO 3
<211> LENGTH: 54
<212> TYPE: DNA
<213> ORGANISM: Artificial Sequence
<220> FEATURE:
<223> OTHER INFORMATION: ApoE tandem repeat (ApoEII)

<400> SEQUENCE: 3
ctgagaaagc tgcggaagcg gctgctgctg aggaagctga gaaaagact gctg           54

<210> SEQ ID NO 4
<211> LENGTH: 63
<212> TYPE: DNA
<213> ORGANISM: Artificial Sequence
<220> FEATURE:
<223> OTHER INFORMATION: Linker

<400> SEQUENCE: 4
ctgggagggg gaggatctgg cggaggcgga agtggcggcg aggatcagg gggcggaggc     60 tct                                                                  63

<210> SEQ ID NO 5
<211> LENGTH: 550
<212> TYPE: PRT
<213> ORGANISM: Artificial Sequence
<220> FEATURE:
<223> OTHER INFORMATION: coIDS

<400> SEQUENCE: 5
```

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro

-continued

```
            145                 150                 155                 160
        Ser Ser Glu Lys Tyr Glu Asn Thr Lys Thr Cys Arg Gly Pro Asp Gly
                        165                 170                 175

Glu Leu His Ala Asn Leu Leu Cys Pro Val Asp Val Leu Asp Val Pro
                        180                 185                 190

Glu Gly Thr Leu Pro Asp Lys Gln Ser Thr Glu Gln Ala Ile Gln Leu
                        195                 200                 205

Leu Glu Lys Met Lys Thr Ser Ala Ser Pro Phe Phe Leu Ala Val Gly
                        210                 215                 220

Tyr His Lys Pro His Ile Pro Phe Arg Tyr Pro Lys Glu Phe Gln Lys
        225                 230                 235                 240

Leu Tyr Pro Leu Glu Asn Ile Thr Leu Ala Pro Asp Pro Glu Val Pro
                        245                 250                 255

Asp Gly Leu Pro Pro Val Ala Tyr Asn Pro Trp Met Asp Ile Arg Gln
                        260                 265                 270

Arg Glu Asp Val Gln Ala Leu Asn Ile Ser Val Pro Tyr Gly Pro Ile
                        275                 280                 285

Pro Val Asp Phe Gln Arg Lys Ile Arg Gln Ser Tyr Phe Ala Ser Val
                        290                 295                 300

Ser Tyr Leu Asp Thr Gln Val Gly Arg Leu Leu Ser Ala Leu Asp Asp
        305                 310                 315                 320

Leu Gln Leu Ala Asn Ser Thr Ile Ile Ala Phe Thr Ser Asp His Gly
                        325                 330                 335

Trp Ala Leu Gly Glu His Gly Glu Trp Ala Lys Tyr Ser Asn Phe Asp
                        340                 345                 350

Val Ala Thr His Val Pro Leu Ile Phe Tyr Val Pro Gly Arg Thr Ala
                        355                 360                 365

Ser Leu Pro Glu Ala Gly Glu Lys Leu Phe Pro Tyr Leu Asp Pro Phe
                        370                 375                 380

Asp Ser Ala Ser Gln Leu Met Glu Pro Gly Arg Gln Ser Met Asp Leu
        385                 390                 395                 400

Val Glu Leu Val Ser Leu Phe Pro Thr Leu Ala Gly Leu Ala Gly Leu
                        405                 410                 415

Gln Val Pro Pro Arg Cys Pro Val Pro Ser Phe His Val Glu Leu Cys
                        420                 425                 430

Arg Glu Gly Lys Asn Leu Leu Lys His Phe Arg Phe Arg Asp Leu Glu
                        435                 440                 445

Glu Asp Pro Tyr Leu Pro Gly Asn Pro Arg Glu Leu Ile Ala Tyr Ser
                        450                 455                 460

Gln Tyr Pro Arg Pro Ser Asp Ile Pro Gln Trp Asn Ser Asp Lys Pro
        465                 470                 475                 480

Ser Leu Lys Asp Ile Lys Ile Met Gly Tyr Ser Ile Arg Thr Ile Asp
                        485                 490                 495

Tyr Arg Tyr Thr Val Trp Val Gly Phe Asn Pro Asp Glu Phe Leu Ala
                        500                 505                 510

Asn Phe Ser Asp Ile His Ala Gly Glu Leu Tyr Phe Val Asp Ser Asp
                        515                 520                 525

Pro Leu Gln Asp His Asn Met Tyr Asn Asp Ser Gln Gly Gly Asp Leu
                        530                 535                 540

Phe Gln Leu Leu Met Pro
        545                 550

<210> SEQ ID NO 6
```

```
<211> LENGTH: 550
<212> TYPE: PRT
<213> ORGANISM: Homo sapiens

<400> SEQUENCE: 6
```

| | | | | | | | | | | | | | | |
|---|---|---|---|---|---|---|---|---|---|---|---|---|---|---|
| Met | Pro | Pro | Pro | Arg | Thr | Gly | Arg | Gly | Leu | Leu | Trp | Leu | Gly | Leu | Val |
| 1 | | | | 5 | | | | | 10 | | | | | 15 | |
| Leu | Ser | Ser | Val | Cys | Val | Ala | Leu | Gly | Ser | Glu | Thr | Gln | Ala | Asn | Ser |
| | | | 20 | | | | | 25 | | | | | 30 | | |
| Thr | Thr | Asp | Ala | Leu | Asn | Val | Leu | Leu | Ile | Ile | Val | Asp | Asp | Leu | Arg |
| | | 35 | | | | | 40 | | | | | 45 | | | |
| Pro | Ser | Leu | Gly | Cys | Tyr | Gly | Asp | Lys | Leu | Val | Arg | Ser | Pro | Asn | Ile |
| | 50 | | | | | 55 | | | | | 60 | | | | |
| Asp | Gln | Leu | Ala | Ser | His | Ser | Leu | Leu | Phe | Gln | Asn | Ala | Phe | Ala | Gln |
| 65 | | | | | 70 | | | | | 75 | | | | | 80 |
| Gln | Ala | Val | Cys | Ala | Pro | Ser | Arg | Val | Ser | Phe | Leu | Thr | Gly | Arg | Arg |
| | | | | 85 | | | | | 90 | | | | | 95 | |
| Pro | Asp | Thr | Thr | Arg | Leu | Tyr | Asp | Phe | Asn | Ser | Tyr | Trp | Arg | Val | His |
| | | | 100 | | | | | 105 | | | | | 110 | | |
| Ala | Gly | Asn | Phe | Ser | Thr | Ile | Pro | Gln | Tyr | Phe | Lys | Glu | Asn | Gly | Tyr |
| | | | 115 | | | | | 120 | | | | | 125 | | |
| Val | Thr | Met | Ser | Val | Gly | Lys | Val | Phe | His | Pro | Gly | Ile | Ser | Ser | Asn |
| | 130 | | | | | 135 | | | | | 140 | | | | |
| His | Thr | Asp | Asp | Ser | Pro | Tyr | Ser | Trp | Ser | Phe | Pro | Pro | Tyr | His | Pro |
| 145 | | | | | 150 | | | | | 155 | | | | | 160 |
| Ser | Ser | Glu | Lys | Tyr | Glu | Asn | Thr | Lys | Thr | Cys | Arg | Gly | Pro | Asp | Gly |
| | | | | 165 | | | | | 170 | | | | | 175 | |
| Glu | Leu | His | Ala | Asn | Leu | Leu | Cys | Pro | Val | Asp | Val | Leu | Asp | Val | Pro |
| | | | 180 | | | | | 185 | | | | | 190 | | |
| Glu | Gly | Thr | Leu | Pro | Asp | Lys | Gln | Ser | Thr | Glu | Gln | Ala | Ile | Gln | Leu |
| | | | 195 | | | | | 200 | | | | | 205 | | |
| Leu | Glu | Lys | Met | Lys | Thr | Ser | Ala | Ser | Pro | Phe | Phe | Leu | Ala | Val | Gly |
| | 210 | | | | | 215 | | | | | 220 | | | | |
| Tyr | His | Lys | Pro | His | Ile | Pro | Phe | Arg | Tyr | Pro | Lys | Glu | Phe | Gln | Lys |
| 225 | | | | | 230 | | | | | 235 | | | | | 240 |
| Leu | Tyr | Pro | Leu | Glu | Asn | Ile | Thr | Leu | Ala | Pro | Asp | Pro | Glu | Val | Pro |
| | | | | 245 | | | | | 250 | | | | | 255 | |
| Asp | Gly | Leu | Pro | Pro | Val | Ala | Tyr | Asn | Pro | Trp | Met | Asp | Ile | Arg | Gln |
| | | | 260 | | | | | 265 | | | | | 270 | | |
| Arg | Glu | Asp | Val | Gln | Ala | Leu | Asn | Ile | Ser | Val | Pro | Tyr | Gly | Pro | Ile |
| | | 275 | | | | | 280 | | | | | 285 | | | |
| Pro | Val | Asp | Phe | Gln | Arg | Lys | Ile | Arg | Gln | Ser | Tyr | Phe | Ala | Ser | Val |
| | 290 | | | | | 295 | | | | | 300 | | | | |
| Ser | Tyr | Leu | Asp | Thr | Gln | Val | Gly | Arg | Leu | Leu | Ser | Ala | Leu | Asp | Asp |
| 305 | | | | | 310 | | | | | 315 | | | | | 320 |
| Leu | Gln | Leu | Ala | Asn | Ser | Thr | Ile | Ile | Ala | Phe | Thr | Ser | Asp | His | Gly |
| | | | | 325 | | | | | 330 | | | | | 335 | |
| Trp | Ala | Leu | Gly | Glu | His | Gly | Glu | Trp | Ala | Lys | Tyr | Ser | Asn | Phe | Asp |
| | | | 340 | | | | | 345 | | | | | 350 | | |
| Val | Ala | Thr | His | Val | Pro | Leu | Ile | Phe | Tyr | Val | Pro | Gly | Arg | Thr | Ala |
| | | | 355 | | | | | 360 | | | | | 365 | | |
| Ser | Leu | Pro | Glu | Ala | Gly | Glu | Lys | Leu | Phe | Pro | Tyr | Leu | Asp | Pro | Phe |
| | 370 | | | | | 375 | | | | | 380 | | | | |
| Asp | Ser | Ala | Ser | Gln | Leu | Met | Glu | Pro | Gly | Arg | Gln | Ser | Met | Asp | Leu |

```
                385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
                420                 425                 430

Arg Glu Gly Lys Asn Leu Leu Lys His Phe Arg Phe Arg Asp Leu Glu
                435                 440                 445

Glu Asp Pro Tyr Leu Pro Gly Asn Pro Arg Glu Leu Ile Ala Tyr Ser
                450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
                500                 505                 510

Asn Phe Ser Asp Ile His Ala Gly Glu Leu Tyr Phe Val Asp Ser Asp
                515                 520                 525

Pro Leu Gln Asp His Asn Met Tyr Asn Asp Ser Gln Gly Gly Asp Leu
                530                 535                 540

Phe Gln Leu Leu Met Pro
545                 550

<210> SEQ ID NO 7
<211> LENGTH: 18
<212> TYPE: PRT
<213> ORGANISM: Artificial Sequence
<220> FEATURE:
<223> OTHER INFORMATION: ApoE tandem repeat (ApoEII)

<400> SEQUENCE: 7

Leu Arg Lys Leu Arg Lys Arg Leu Leu Leu Arg Lys Leu Arg Lys Arg
1               5                   10                  15

Leu Leu

<210> SEQ ID NO 8
<211> LENGTH: 21
<212> TYPE: PRT
<213> ORGANISM: Artificial Sequence
<220> FEATURE:
<223> OTHER INFORMATION: Linker

<400> SEQUENCE: 8

Leu Gly Gly Gly Gly Ser Gly Gly Gly Gly Ser Gly Gly Gly Gly Ser
1               5                   10                  15

Gly Gly Gly Gly Ser
            20
```

GENE THERAPY

TECHNICAL FIELD OF THE INVENTION

The present invention relates to stem cell gene therapies for the treatment of mucopolysaccharidosis (MPS) II.

BACKGROUND TO THE INVENTION

Mucopolysaccharidosis type II (MPS II, OMIM #309900), or Hunter syndrome, is a paediatric X-linked lysosomal storage disorder caused by mutations in the IDS gene, leading to deficiencies in iduronate-2-sulfatase enzyme (EC 3.1.6.13). This IDS enzyme insufficiency, in turn, affects the catabolism of both heparan sulphate (HS) and dermatan sulphate, subsequently leading to their unregulated accumulation in the lysosomal compartment of all cells (1). MPS II affects 1.3 per 100,000 male live births (2-4) and has historically been classified as either attenuated or severe. Recently however, most clinical perspectives have described a continuum between two extremes, depending on the severity of symptoms (4). MPS II is a chronic and progressive multi-system disease affecting a multitude of organs such as the brain, heart, skeleton and joints. Clinical manifestations in the milder forms of MPS II include severe skeletal abnormalities, known as dysostosis multiplex, short stature, joint stiffness, and hepatosplenomegaly, accompanied by cardiorespiratory symptoms (4, 5). Severe MPS II additionally features progressive neurodegeneration, followed by death in teenage years due to obstructive airway disease and cardiac failure (4, 6, 7).

Enzyme replacement therapy (ERT), where exogenous replacement enzyme is delivered intravenously and internalised by cells using the mannose-6-phosphate receptor, has been used to treat the somatic symptoms in MPS II patients regardless of disease severity (8, 9). However, enzyme circulating in the bloodstream is prevented from reaching the CNS by the blood-brain barrier (BBB), considerably reducing therapeutic benefits for the two-thirds of MPS II patients that are cognitively affected. Moreover, severe anaphylactic reactions to the replacement enzyme have been reported (9, 10), as well as neutralizing antibodies to the enzyme (11), which may decrease efficacy of the treatment (12).

No current therapy has been specifically designed and approved to treat the neurological symptoms in MPS II, although a wide variety of strategies are in development. In particular, gene therapy is an attractive therapeutic possibility for a monogenic disorder such as MPS II. Stem cell gene therapy using second-generation lentiviral vectors (LV) (13) and direct injection of various adeno-associated vectors (AAV) into the CNS (5, 14, 15) have yielded promising results. However, scale up from the mouse brain to the human brain is the primary hurdle, as is adequate distribution of the therapeutic vector throughout brain tissue.

Allogeneic stem cell transplantation, although recommended to treat neurological symptoms in MPS I Hurler (16-18), has been highly variable in treating the CNS in MPS II and is associated with high rates of morbidity and mortality primarily caused by rejection and graft-versus-host disease (19, 20). It has been suggested that the level of enzyme delivered from an allogeneic transplant, although sufficient to clear primary storage material in peripheral organs, may be too low in the brain and is therefore the limiting factor for complete neurological correction (21, 22). Indeed, supra-physiological enzyme levels in LV-transduced haematopoietic stem and progenitor cells (HSPCs) and their progeny have been shown to correct neurologic disease manifestations in metachromatic leukodystrophy, MPS I and MPS IIIA (21, 23-25). This leads to a reconstitution of the recipient's macrophage and microglia populations by cells derived from genetically-modified donor HSPCs, which synthesise and secrete lysosomal enzyme to cross-correct neighbouring cells (22). Moreover, corrected microglial cells that originate from myeloid progenitors may also significantly contribute to the turnover of CNS microglia, although controversy exists regarding their maintenance and renewal in adult CNS.

The degree of efficacy of stem cell gene therapy approaches to treat the CNS seems to rely heavily on the level of enzyme produced and secreted from HSCs and their progeny (22, 23). High levels of enzyme are generally found in the bloodstream, but are prevented from entering the CNS by the dense microvasculature of the BBB (26).

The primary hurdle in treating the neuropathology of diseases that involve the CNS is to bypass the BBB. One such strategy is to target proteins to translocate to the CNS via a process known as transcytosis, which exploits receptors located on the BBB surface, such as the transferrin receptor (TfR) and low-density lipoprotein receptor (LDLR) (27). The LDLR family are cell-surface receptors that bind alipoprotein (Apo) complexes and target them to the lysosomes (28). Apo complexes bind LDLR on the surface of the BBB and are transcytosed to the abluminal side before being released prior to uptake into neurons and astrocytes (29). A number of studies have exploited this minimally-invasive technology by fusing LDLR-binding domain peptides to enzymes of interest, and shown efficient delivery of these chimeric constructs across the BBB in animal models (29-33).

We sought to harness this technology to efficiently treat brain pathology and cognitive decline in MPS II by fusing the receptor-binding domain of human alipoprotein E (ApoE) as a tandem repeat to the IDS gene by means of an invariant flexible linker at the C-terminal in a $3^{rd}$-generation lentiviral vector. This allows HSPCs that are corrected ex vivo to express supra-physiological levels of IDS enzyme that may preferentially bypass the BBB in transplanted animals, thereby increasing the levels of enzyme that reach brain parenchyma from the bloodstream.

It is an object of the present invention to overcome one or more of the problems associated with the above proposed therapies for MPSII. It is also an object of the present invention to provide an effective treatment for MPSII. Such a treatment would ideally be relatively easy to administer and have a low toxicological profile. It would also be desirable if such a treatment was able to overcome or obviate issues concerned with administering treatments which need to cross the blood brain barrier.

SUMMARY OF INVENTION

In accordance with an aspect of the present invention, there is provided a nucleic acid comprising an iduronate-2-sulfatase (IDS) gene sequence and a repeat of the Apolipoprotein E (ApoEII) gene sequence, or a repeat of part of the ApoEII gene sequence.

The nucleic acid may further comprise an intervening linker sequence located between the IDS sequence and the ApoEII sequence.

The IDS sequence may be a codon-optimised sequence of the wild-type IDS sequence.

The repeat of the ApoEII sequence may be in the form of a tandem repeat. The repeat of the ApoEII sequence may be upstream and/or downstream of the IDS sequence.

The IDS sequence may comprise the sequence according to SEQ ID No. 1 or SEQ ID No. 2 or a derivative sequence having at least 90% homology thereof. Where the sequence is a derivative sequence, preferably it has at least 93% homology thereof. Even more preferred, the sequence may be a derivative sequence having at least 95%, at least 96%, at least 97%, at least 98% or at least 99% homology with SEQ ID No. 1 or SEQ ID No. 2.

The ApoEII sequence may comprise one or more sequences according to SEQ ID No. 3 or a derivative sequence having at least 95%, at least 96%, at least 97%, at least 98% or at least 99% homology thereof.

The intervening linker sequence may comprise the sequence according to SEQ ID No. 4 or a derivative sequence having at least 95%, at least 96%, at least 97%, at least 98% or at least 99% homology thereof.

In accordance with another aspect of the present invention, there is provided a nucleic acid for use in increasing the plasma level, or stability in plasma, of an enzyme in an individual, the nucleic acid comprising an enzyme gene sequence and a repeat of the Apolipoprotein E (ApoEII) gene sequence.

The nucleic acid may further comprise an intervening linker sequence located between the enzyme sequence and the ApoEII sequence.

The enzyme sequence may be a codon-optimised sequence of the enzyme sequence.

The repeat of the ApoEII sequence may be in the form of a tandem repeat. The repeat of the ApoEII sequence may be upstream and/or downstream of the enzyme sequence.

The ApoEII sequence may comprise one or more sequences according to SEQ ID No. 3 or a derivative sequence having at least 95%, at least 96%, at least 97%, at least 98% or at least 99% homology thereof.

The intervening linker sequence may comprise the sequence according to SEQ ID No. 4 or a derivative sequence having at least 95%, at least 96%, at least 97%, at least 98% or at least 99% homology thereof.

The enzyme may be one which is deficient or present at low plasma levels in individuals suffering from lysosomal storage disease. The lysosomal storage disease may comprise Mucopolysaccharidosis type II (MPS II).

The nucleic acid may be a DNA, RNA, cDNA, or PNA and may be recombinant or synthetic. It may be single stranded or double stranded. The nucleic acid sequence may be derived by cloning, for example using standard molecular cloning techniques including restriction digestion, ligation, gel electrophoresis (for example as described in Sambrook et al; *Molecular Cloning: A laboratory manual*, Cold Spring Harbour laboratory Press). The nucleic acid sequence may be isolated or amplified using PCR technology. Such technology may employ primers based upon the sequence of the nucleic acid sequence to be amplified. With the sequence information provided, the skilled person can use available cloning techniques to produce a nucleic acid sequence or vector suitable for transduction into a cell.

The codon optimised IDS nucleic acid sequence may be optimised in a number of ways so as to enable enhanced expression or activity. For example the sequence may have been optimised by selecting codons most common in human cells and/or reducing one or more secondary structures and hairpins which may arise in subsequently formed mRNA and/or inserting a Kozak sequence at the ATG start site.

Preferably, the nucleic acid sequence is provided with, in or as part of an expression vector. Preferably, it may be provided as a gene therapy vector, preferably which is suitable for ex vivo transduction in haematopoietic stem and progenitor cells (HSPCs) which are subsequently returned to a mammalian body for expression. The vector may be viral or non-viral (e.g. a plasmid). Viral vectors include those derived from lentivirus, adenovirus, adenoassociated virus (AAV) including mutated forms, retrovirus, herpes virus, vaccinia virus, MMLV, GaLV, Simian Immune Deficiency Virus (SIV), HIV, pox virus, and SV40. A viral vector is preferably replication defective, although it is envisaged that it may be replication deficient, replication competent or conditional. A viral vector may typically persist in an extrachromosomal state without integrating into the genome of the target neural cells. A preferred viral vector is a lentivirus vector. The viral vector may be modified to delete any non-essential sequences and these will be apparent to the skilled addressee.

The viral vector has the ability to enter a cell. However, a non-viral vector such as a plasmid may be complexed with an agent to facilitate its uptake by a target cell. Such agents include polycationic agents. Alternatively, a delivery system such as a liposome based delivery system may be used.

The vector for use in the present invention is preferably suitable for use in or ex vivo or in vitro, and is preferably suitable for use in a human. Most preferably, the vector is suitable for transducing haematopoietic stem and progenitor cells (HSPCs) ex vivo.

The vector will preferably comprise one or more regulatory sequences to direct expression of the nucleic acid. A regulatory sequence may include a promoter operably linked to the IDS and ApoEII nucleic acid sequence, an enhancer, a transcription termination signal, a polyadenylation sequence, an origin of replication, a nucleic acid restriction site, and a homologous recombination site. A vector may also include a selectable marker, for example to determine expression of the vector in a growth system (for example a bacterial cell) or in a target cell.

By "operably linked" means that the nucleic acid sequence is functionally associated with the sequence to which it is operably linked, such that they are linked in a manner such that they affect the expression or function of one another. For example, a nucleic acid sequence operably linked to a promoter will have an expression pattern influenced by the promoter.

In accordance with an aspect of the present invention, there is provided haematopoietic stem and progenitor cells (HSPCs) for use in the treatment, management, retardation of progression or normalisation of development of an iduronate-2-sulfatase (IDS) deficiency and/or Mucopolysaccharidosis type II (MPS II) in an individual, wherein the HSPCs are removed from the patient, transduced ex vivo with the nucleic acid as herein above described, and the transduced HSPCs are administered to the individual.

In accordance with a related aspect of the present invention, there is provided haematopoietic stem and progenitor cells (HSPCs) for use in a method of, or for the, treatment, management, retardation of progression or normalisation of development of an iduronate-2-sulfatase (IDS) deficiency and/or Mucopolysaccharidosis type II (MPS II) in an individual, wherein the HSPCs have been removed from the patient, transduced ex vivo with the nucleic acid as herein above described, and the transduced HSPCs administered to the individual.

In accordance with a related aspect of the present invention, there is provided haematopoietic stem and progenitor cells (HSPCs) for use in a method of treatment, management, retardation of progression or normalisation of development of an iduronate-2-sulfatase (IDS) deficiency and/or Mucopolysaccharidosis type II (MPS II) in an individual, wherein the method comprises identifying an individual having said iduronate-2-sulfatase (IDS) deficiency and/or in need of elevated iduronate-2-sulfatase (IDS) levels, removing a portion of HSPCs from the individual, transduced the HSPCs ex vivo with the nucleic acid as herein above described and administering a therapeutically effective amount of the transduced HSPCs to the individual.

In accordance with a related invention, there is provided haematopoietic stem and progenitor cells (HSPCs) for use in the manufacture of a medicament for treating, managing, retarding progression or normalising development of a disease or condition attributable to iduronate-2-sulfatase (IDS) deficiency, wherein the HSPCs have been removed from the patient, transduced ex vivo with the nucleic acid as herein above described, and the transduced HSPCs formed into a medicament for administration to the patient.

Whilst the above HSPCs aspects are preferably utilising autologous HSPCs (where they have first been removed from the patient or individual), allogeneic HSPCs may also be utilised, therefore removing the need that the HSPCs be removed from the patient or individual, transduced ex vivo and then administered to the patient or individual. Allogeneic HSPCs may be derived from cord blood.

In accordance with an aspect of the present invention, there is provided a composition comprising:
a) a first moiety comprising iduronate-2-sulfatase (IDS); and
b) a second moiety comprising a repeat of Apolipoprotein E (ApoEII).

The repeat of ApoEII may be in the form of a tandem repeat. The second moiety may be upstream and/or downstream of the first moiety.

The first and second moiety may have an intervening linker moiety located there between.

The amino acid sequence of the first moiety may comprise the sequence according to SEQ ID No. 5 or a derivative sequence having at least 90% homology thereof. Where the sequence is a derivative sequence, preferably it has at least 93% homology thereof. Even more preferred, the sequence may be a derivative sequence having at least 95%, at least 96%, at least 97%, at least 98% or at least 99% homology with SEQ ID No. 5.

The amino acid sequence of the second moiety may comprise one or more sequences according to SEQ ID No. 7 or a derivative sequence having at least 95%, at least 96%, at least 97%, at least 98% or at least 99% homology thereof.

The amino acid sequence of the intervening linker moiety may comprise the sequence according to SEQ ID No. 8 or a derivative sequence having at least 95%, at least 96%, at least 97%, at least 98% or at least 99% homology thereof.

In accordance with a further aspect of the present invention, there is provided a composition for increasing the plasma level, or stability in plasma, of an enzyme comprising:
a) a first moiety comprising the enzyme; and
b) a second moiety comprising a repeat of Apolipoprotein E (ApoEII).

The repeat of ApoEII may be in the form of a tandem repeat. The second moiety may be upstream and/or downstream of the first moiety.

The first and second moiety may have an intervening linker moiety located there between.

Advantageously, the inventors have found that they are able to increase the activity in plasma of enzymes, suggesting potential alterations in enzyme stability and circulation time, secretion or uptake into cells by including a tandem repeat of ApoEII via a linker to the enzyme.

In a further aspect of the present invention, there is provided a composition comprising a nucleic acid according to SEQ ID No. 1 or a derivative sequence having at least 95% homology thereof.

The composition may comprise a derivative sequence having at least 96%, at least 97%, at least 98% or at least 99% homology thereof.

The composition may be for use in the treatment, management, retardation of progression or normalisation of development of an iduronate-2-sulfatase (IDS) deficiency and/or Mucopolysaccharidosis type II (MPS II) in an individual.

In another aspect of the present invention, there is provided a polypeptide or nucleic acid for use in the treatment, management, retardation of progression or normalisation of development of an iduronate-2-sulfatase (IDS) deficiency and/or Mucopolysaccharidosis type II (MPS II) in an individual, wherein the polypeptide comprises iduronate-2-sulfatase (IDS) tethered to a tandem repeat of Apolipoprotein E (ApoEII) or the nucleic acid comprises an iduronate-2-sulfatase (IDS) gene sequence tethered to a tandem repeat of the Apolipoprotein E (ApoEII) gene sequence.

The polypeptide or nucleic acid may be tethered by means of a linker or a linker sequence.

The tandem repeat of ApoEII may be upstream and/or downstream of the IDS.

The IDS gene sequence may be a codon-optimised sequence of the wild-type IDS gene sequence.

The IDS may comprise the amino acid sequence according to SEQ ID No. 5 or a derivative sequence having at least 90% homology thereof. Where the sequence is a derivative sequence, preferably it has at least 93% homology thereof. Even more preferred, the sequence may be a derivative sequence having at least 95%, at least 96%, at least 97%, at least 98% or at least 99% homology with SEQ ID No. 5.

The IDS gene sequence may comprise the sequence according to SEQ ID No. 1 or SEQ ID No. 2 or a derivative sequence having at least 90% homology thereof. Where the sequence is a derivative sequence, preferably it has at least 93% homology thereof. Even more preferred, the sequence may be a derivative sequence having at least 95%, at least 96%, at least 97%, at least 98% or at least 99% homology with SEQ ID No. 1 or SEQ ID No. 2.

The tandem repeat of the Apolipoprotein E (ApoEII) may comprise the amino acid sequence according to SEQ ID No. 7 or a derivative sequence having at least 95%, at least 96%, at least 97%, at least 98% or at least 99% homology thereof. The tandem repeat of the Apolipoprotein E (ApoEII) gene sequence may comprise the amino acid sequence according to SEQ ID No. 3 or a derivative sequence having at least 95%, at least 96%, at least 97%, at least 98% or at least 99% homology thereof.

The linker may comprise the amino acid sequence according to SEQ ID No. 8 or a derivative sequence having at least 95%, at least 96%, at least 97%, at least 98% or at least 99% homology thereof.

The linker sequence may comprise the sequence according to SEQ ID No. 4 or a derivative sequence having at least 95%, at least 96%, at least 97%, at least 98% or at least 99% homology thereof.

The polypeptide or nucleic acid may be associated with or incorporated in a suitable peptide or nucleic acid delivery vehicle or vector.

The term 'gene sequence' is intended to cover nucleic acid sequences generally which are capable to being expressed into the requisite protein, including genomic sequences and sequences where one or more non-coding elements (such as introns) are not present including cDNA.

In all above aspects, the compositions, nucleic acids, vectors, polypeptides and haematopoietic stem and progenitor cells (HSPCs) may be for use in the treatment, management, retardation of progression or normalisation of development of a lysosomal storage disease. Alternatively or additionally, the compositions, nucleic acids, vectors, polypeptides and haematopoietic stem and progenitor cells (HSPCs) may be used in a method of treating, managing, retarding progression or normalising development of a lysosomal storage disease. Alternatively or additionally, the compositions, nucleic acids, vectors, polypeptides and haematopoietic stem and progenitor cells (HSPCs) may be used in a method of treating, managing, retarding progression or normalising development of a lysosomal storage disease, wherein the method comprises identifying a individual having said lysosomal storage disease and/or in need of elevated enzyme levels and administering a therapeutically effective amount of the composition, nucleic acid, vector or polypeptide to said individual. Yet further alternatively or additionally, the compositions, nucleic acids, vectors, polypeptides and haematopoietic stem and progenitor cells (HSPCs) may be for use in the manufacture of a medicament for treating, managing, retarding progression or normalising development of a lysosomal storage disease.

In particular, in all above aspects, the compositions, nucleic acids, vectors, polypeptides and haematopoietic stem and progenitor cells (HSPCs) may be for use in the treatment, management, retardation of progression or normalisation of development of a disease or condition attributable to iduronate-2-sulfatase (IDS) deficiency. Alternatively or additionally, the compositions, nucleic acids, vectors, polypeptides and haematopoietic stem and progenitor cells (HSPCs) may be used in a method of treating, managing, retarding progression or normalising development of a disease or condition attributable to iduronate-2-sulfatase (IDS) deficiency. Alternatively or additionally, the compositions, nucleic acids, vectors, polypeptides and haematopoietic stem and progenitor cells (HSPCs) may be used in a method of treating, managing, retarding progression or normalising development of a disease or condition attributable to iduronate-2-sulfatase (IDS) deficiency, wherein the method comprises identifying a individual having said iduronate-2-sulfatase (IDS) deficiency and/or in need of elevated iduronate-2-sulfatase (IDS) levels and administering a therapeutically effective amount of the composition, nucleic acid, vector or polypeptide to said individual. Yet further alternatively or additionally, the compositions, nucleic acids, vectors, polypeptides and haematopoietic stem and progenitor cells (HSPCs) may be for use in the manufacture of a medicament for treating, managing, retarding progression or normalising development of a disease or condition attributable to iduronate-2-sulfatase (IDS) deficiency. Diseases or conditions attributable to iduronate-2-sulfatase (IDS) deficiencies will include mucopolysaccharidosis type II (MPS II) or Hunters syndrome.

The compositions, nucleic acids, vectors and polypeptides may be a liquid or a solid, for example a powder, gel, or paste. Preferably, a composition, nucleic acid, vectors, polypeptide and haematopoietic stem and progenitor cells (HSPCs) is a liquid, preferably an injectable liquid. Such an injectable liquid will preferably be suitable for intravenous and intracranial administration.

The compositions, nucleic acids, vectors and polypeptides of the preceding aspects of the invention may yet further comprise a pharmaceutically acceptable excipient, adjuvant, diluent or carrier and provide a formulation.

By "pharmaceutically acceptable" is included that the formulation is sterile and pyrogen free. Suitable pharmaceutical carriers are well known in the art of pharmacy. The carrier(s) must be "acceptable" in the sense of being compatible with the agents of the invention and not deleterious to the recipients thereof. Typically, the carriers will be water or saline which will be sterile and pyrogen free; however, other acceptable carriers may be used.

In human therapy, formulations of the invention(s) can be administered alone but will generally be administered in admixture with a suitable pharmaceutical excipient diluent or carrier selected with regard to the intended route of administration and standard pharmaceutical practice.

The formulations of the invention(s) can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In accordance with another aspect of the present invention, there is provided a method for delivering a deficient protein into the brain across the blood brain barrier in an individual suffering from a condition resulting from the deficiency in the protein, the composition comprising a viral vector comprising the gene sequence coding for the deficient protein tethered to a tandem repeat of the Apolipoprotein E (ApoEII) gene sequence, wherein the vector is transduced, ex vivo, with a population of haematopoietic stem and progenitor cells (HSPCs) and the transduced HSPCs administered to the individual where they express the deficient protein in levels sufficient which are sufficient to cross the blood brain barrier.

The vector may comprise a sequence for an invariant flexible linker between the gene sequence coding for the deficient protein and the tandem repeat of the Apolipoprotein E (ApoEII) gene sequence.

The deficient protein may comprise an enzyme. The enzyme may be a lysosomal storage disease enzyme. Preferably, the enzyme comprises iduronate-2-sulfatase (IDS).

In the method, the ApoEII tandem repeat gene sequence may comprise the sequence according to SEQ ID No. 3 or variant sequences having up to 95%, up to 96%, up to 97%, up to 98% or up to 99% homology thereof, whereas the invariant flexible linker sequence may comprise the sequence according to SEQ ID No. 4 or variant sequences having up to 95%, up to 96%, up to 97%, up to 98% or up to 99% homology thereof.

In accordance with yet another aspect of the present invention, there is provided a composition for use in the treatment of a lysosomal storage disease, wherein the composition comprises a viral vector comprising the gene sequence coding for a deficient protein which is implicated in the lysosomal storage disease and which is tethered to a tandem repeat of the Apolipoprotein E (ApoEII) gene sequence.

The vector is preferably transduced, ex vivo, with a population of haematopoietic stem and progenitor cells (HSPCs) and the transduced HSPCs administered to an individual suffering from the lysosomal storage disease.

The vector may comprise a sequence for an invariant flexible linker between the gene sequence coding for the deficient protein and the tandem repeat of the Apolipoprotein E (ApoEII) gene sequence.

The deficient protein may comprise an enzyme. The enzyme may be a lysosomal storage disease enzyme. Preferably, the enzyme comprises iduronate-2-sulfatase (IDS).

The ApoEII tandem repeat gene sequence may comprise the sequence according to SEQ ID No. 3 or variant sequences having up to 95%, up to 96%, up to 97%, up to 98% or up to 99% homology thereof, whereas the invariant flexible linker sequence may comprise the sequence according to SEQ ID No. 4 or variant sequences having up to 95%, up to 96%, up to 97%, up to 98% or up to 99% homology thereof.

In accordance with another aspect of the present invention, there is provided a combination of a nucleic acid comprising an iduronate-2-sulfatase (IDS) gene sequence and a repeat of the Apolipoprotein E (ApoEII) gene sequence and one or more haematopoietic stem and progenitor cells (HSPCs), wherein the nucleic acid is capable of transducing the HSPCs.

The HSPCs will preferably be autologous, that is to say that they are derived from the individual to which the transduced HSPCs are to be administered. Alternatively, the HSPCs may be allogeneic, that is to say that they are derived from a different individual to which the transduced HSPCs are to be administered.

The combination may comprise a nucleic acid as herein above described with respect to earlier aspects and may also be incorporated into a vector as also herein above described.

In another aspect, there is provided a method of preparing a medicament for use in the treatment, management, retardation of progression or normalisation of development of a disease or condition attributable to iduronate-2-sulfatase (IDS) deficiency, the method comprising:
(a) providing one or more HSPCs;
(b) providing a viral vector comprising a sequence coding for IDS tethered to a tandem repeat of the Apolipoprotein E (ApoEII) sequence; and
(c) combining the HSPCs and viral vector under conditions effective enable transduction of the HSPCs with the gene sequence, wherein the transduced HSPCs express IDS.

Preferably, the vector comprises a lentiviral vector and the sequence coding for IDS is tethered to a tandem repeat of the Apolipoprotein E (ApoEII) gene sequence by means of a linker.

In a further aspect, there is provided a method of expressing a deficient protein and/or higher levels of a protein in haematopoietic stem and progenitor cells (HSPCs), the method comprising:
(a) providing one or more HSPCs;
(b) providing a viral vector comprising the sequence coding for the protein tethered to a tandem repeat of the Apolipoprotein E (ApoEII) sequence; and
(c) combining the HSPCs and viral vector under conditions effective to enable transduction of the HSPCs with the sequence.

Preferably, the vector comprises a lentiviral vector and the sequence coding for the protein is tethered to a tandem repeat of the Apolipoprotein E (ApoEII) gene sequence by means of a linker.

Surprisingly, and advantageously, the present inventors have successfully show that by fusing the receptor-binding domain of human alipoprotein E (ApoE) as a tandem repeat to the IDS gene by means of an invariant flexible linker at the C-terminal in a $3^{rd}$-generation lentiviral vector, they efficiently treat brain pathology and cognitive decline in MPS II. This allows HSPCs that are corrected ex vivo to express supra-physiological levels of IDS enzyme that may preferentially bypass the BBB in transplanted animals, thereby increasing the levels of enzyme that reach brain parenchyma from the bloodstream.

Herein reference to "a" or "an" includes within its scope both the singular, and the plural, i.e. one or more.

Unless stated otherwise, the features of each aspect applies to the other aspects of the invention, mutatis mutandis.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and figures), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

DETAILED DESCRIPTION OF THE INVENTION

Aspects and embodiments of the present invention will now be illustrated, by way of example, with reference to the accompanying figures. Further aspects and embodiments will be apparent to those skilled in the art. All documents mentioned in this text are incorporated herein by reference.

Figure 3:
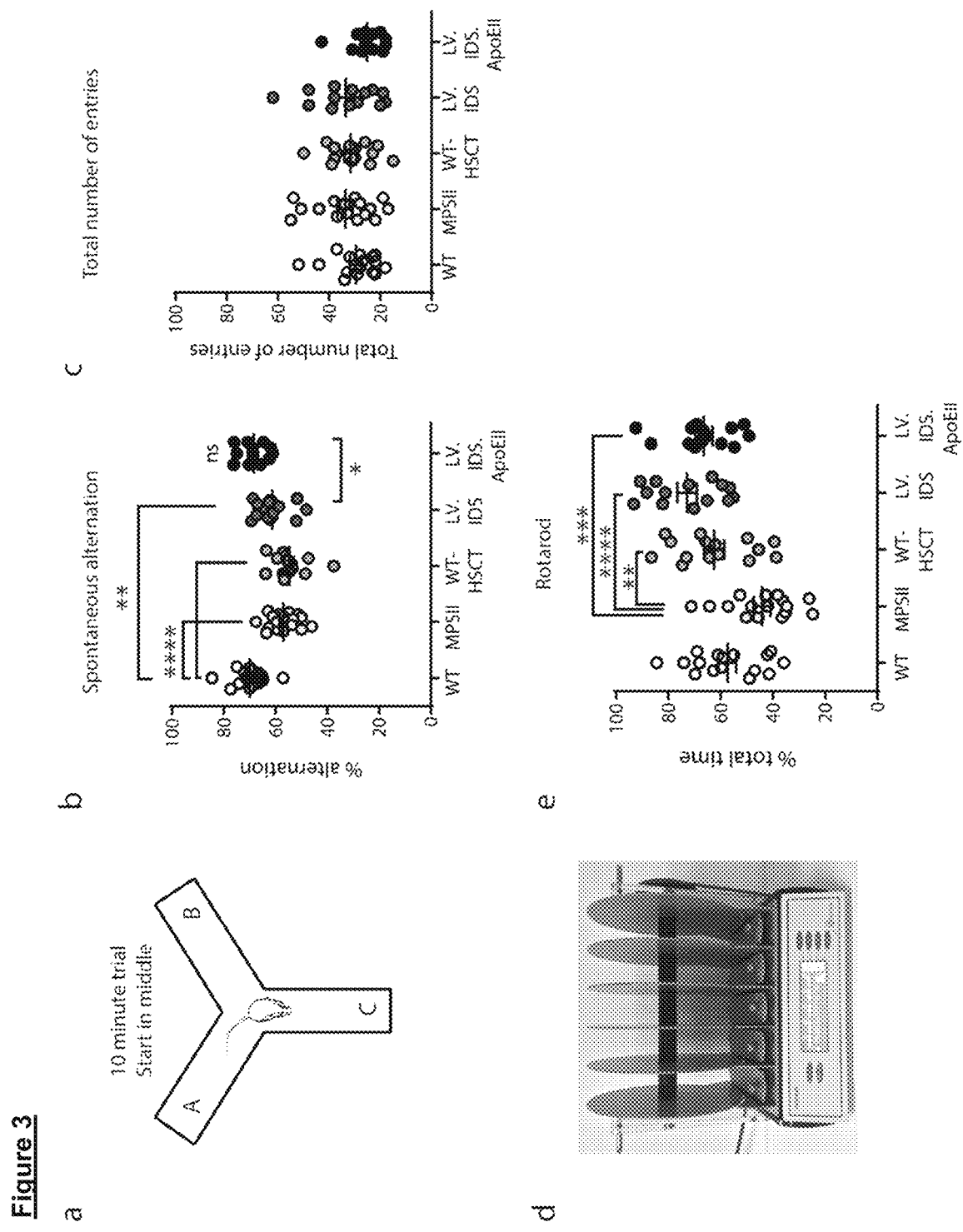
Figure 4:
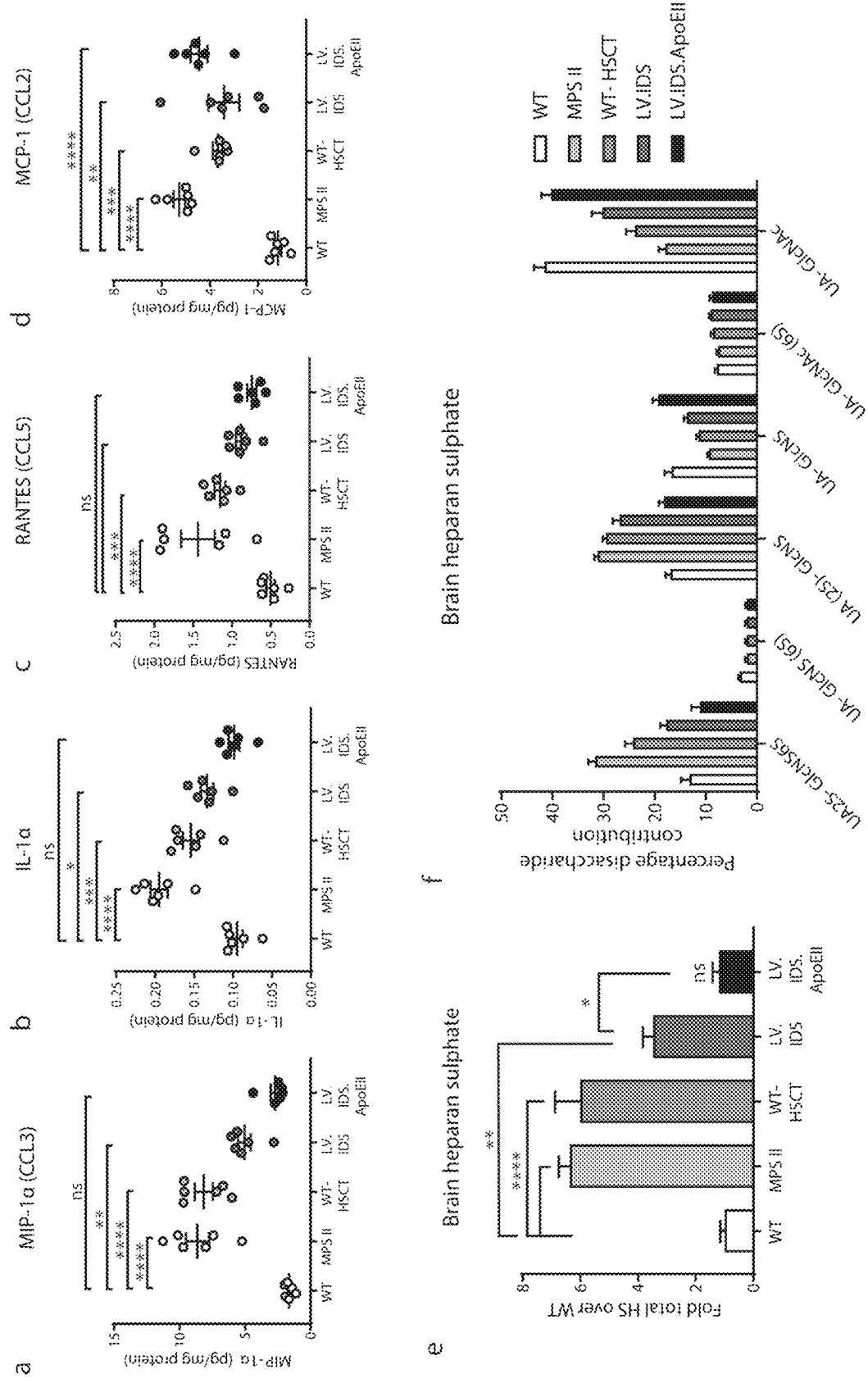
Figure 4:
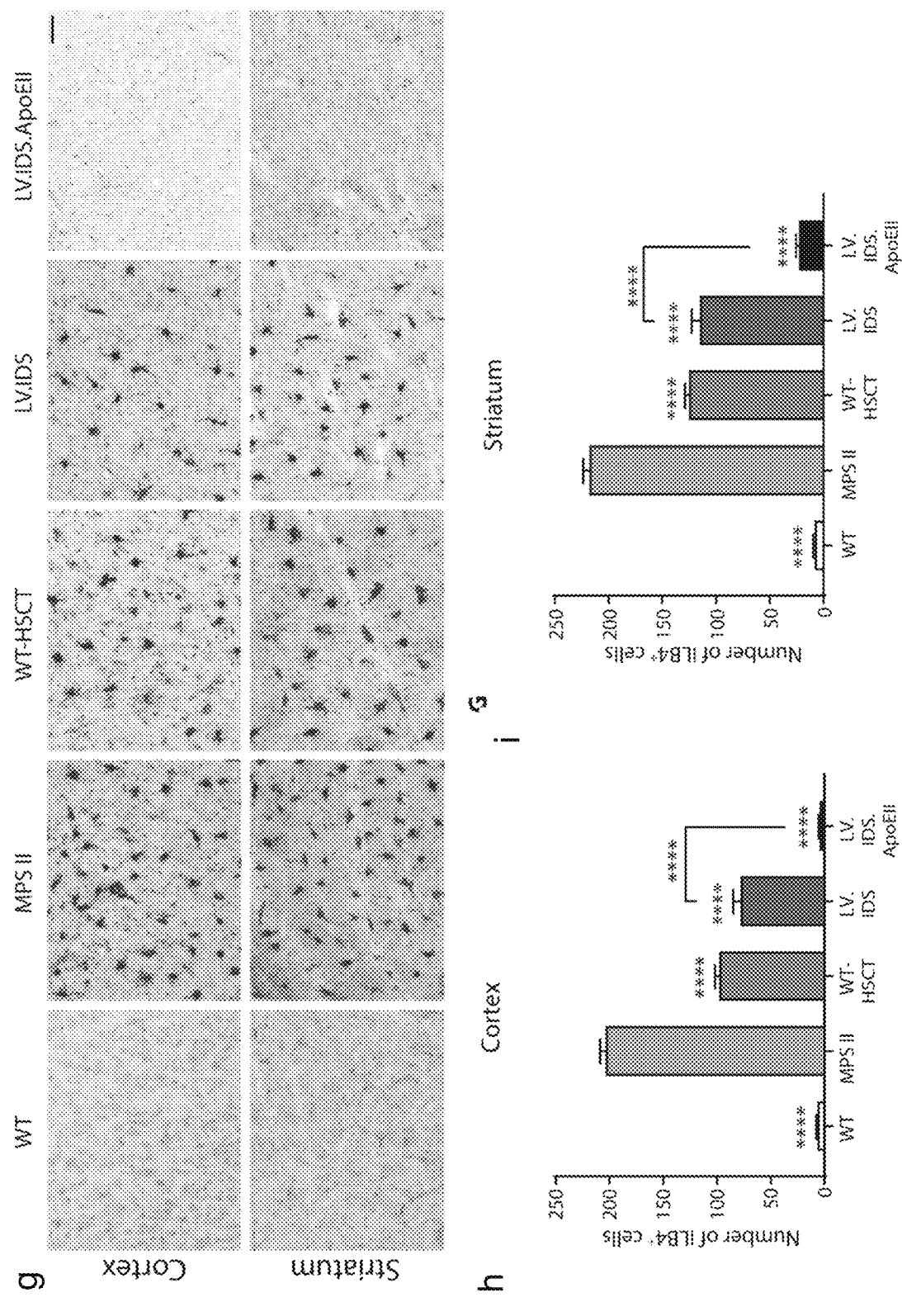
Figure 5:
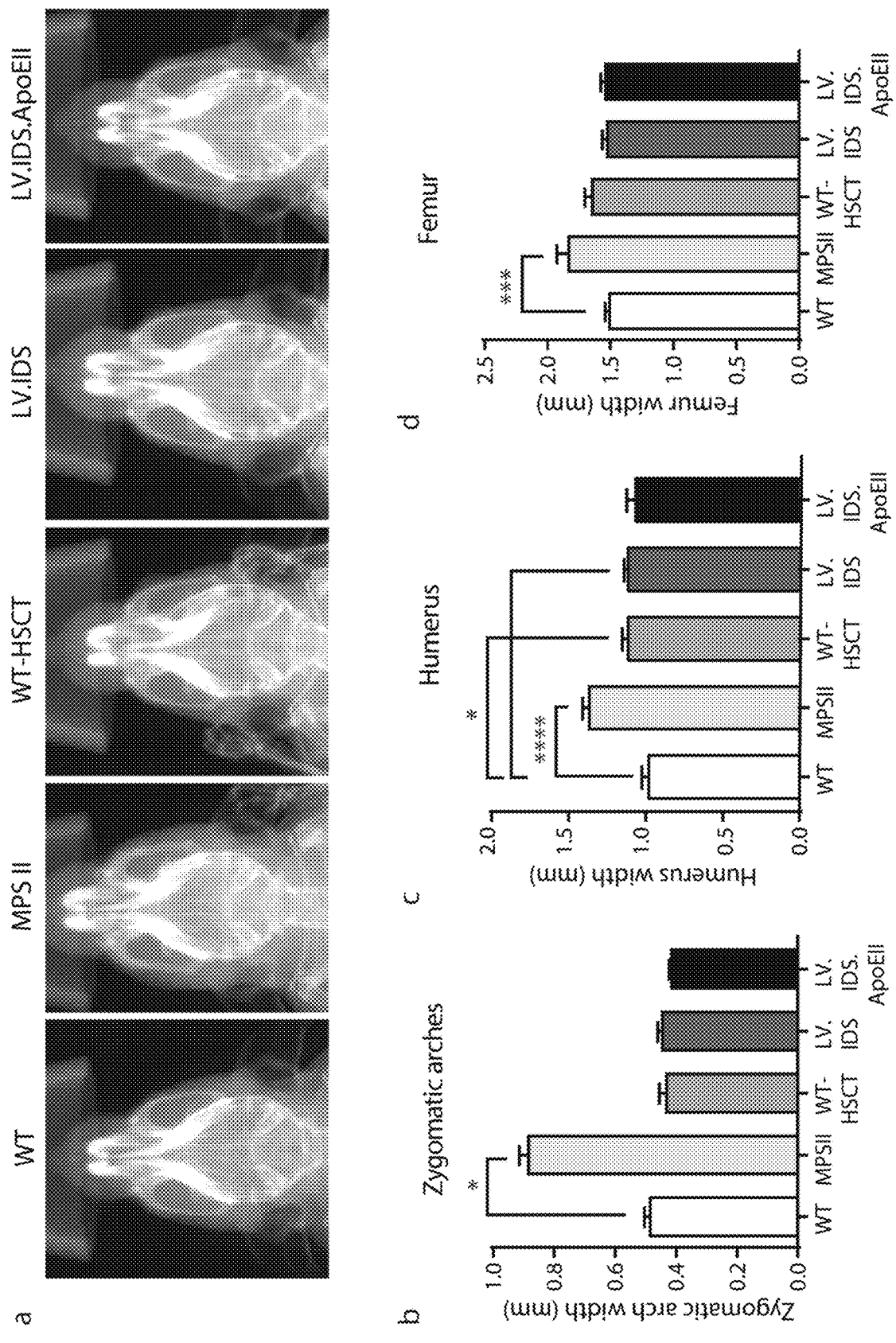
Figure 5:
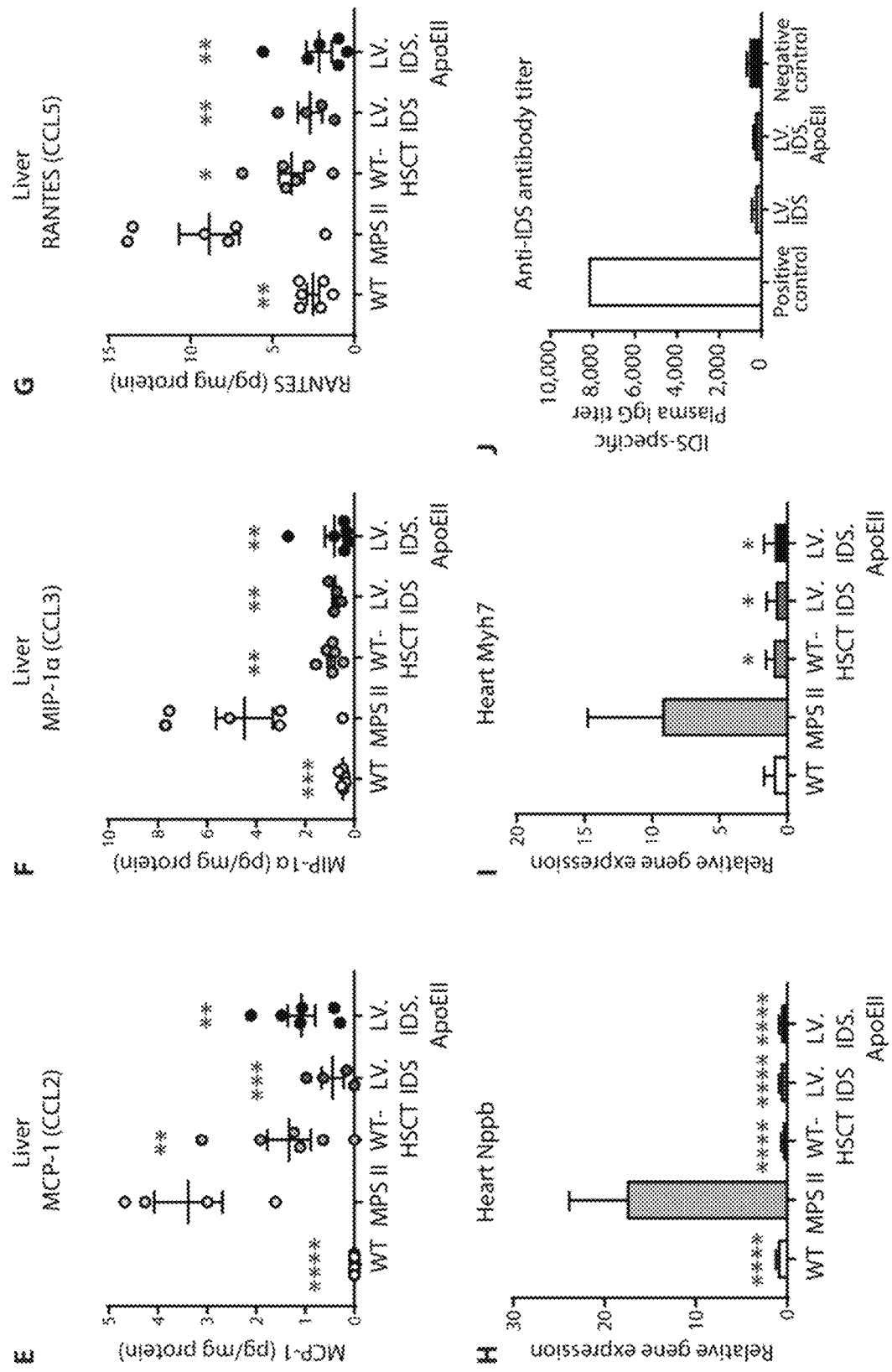
Figure 6:
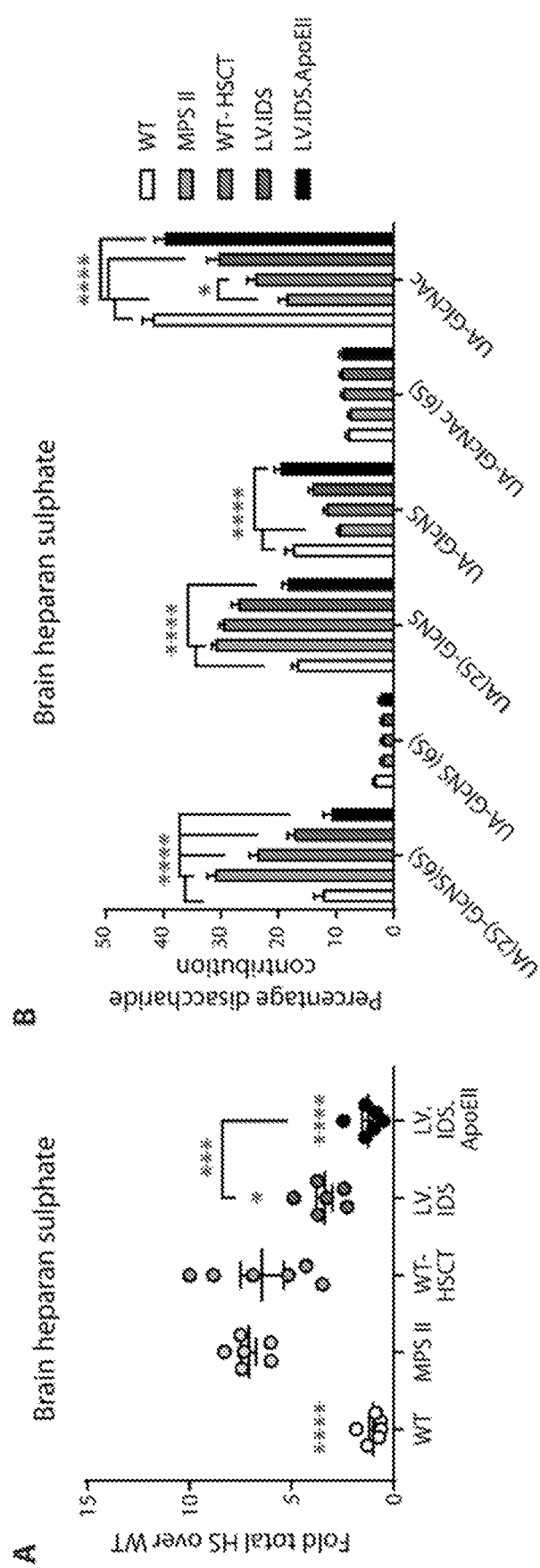
Figure 6:
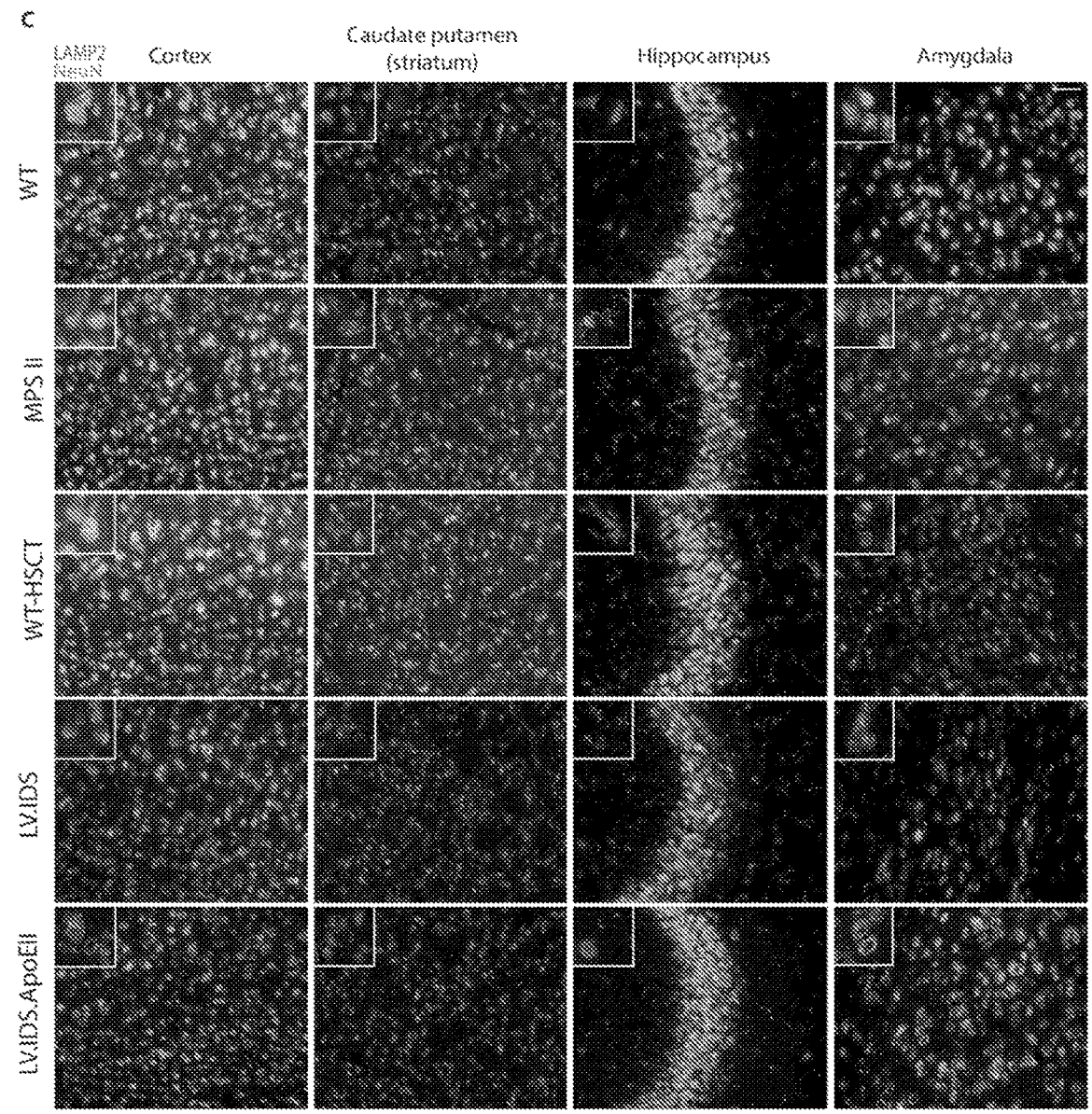
Figure 7:
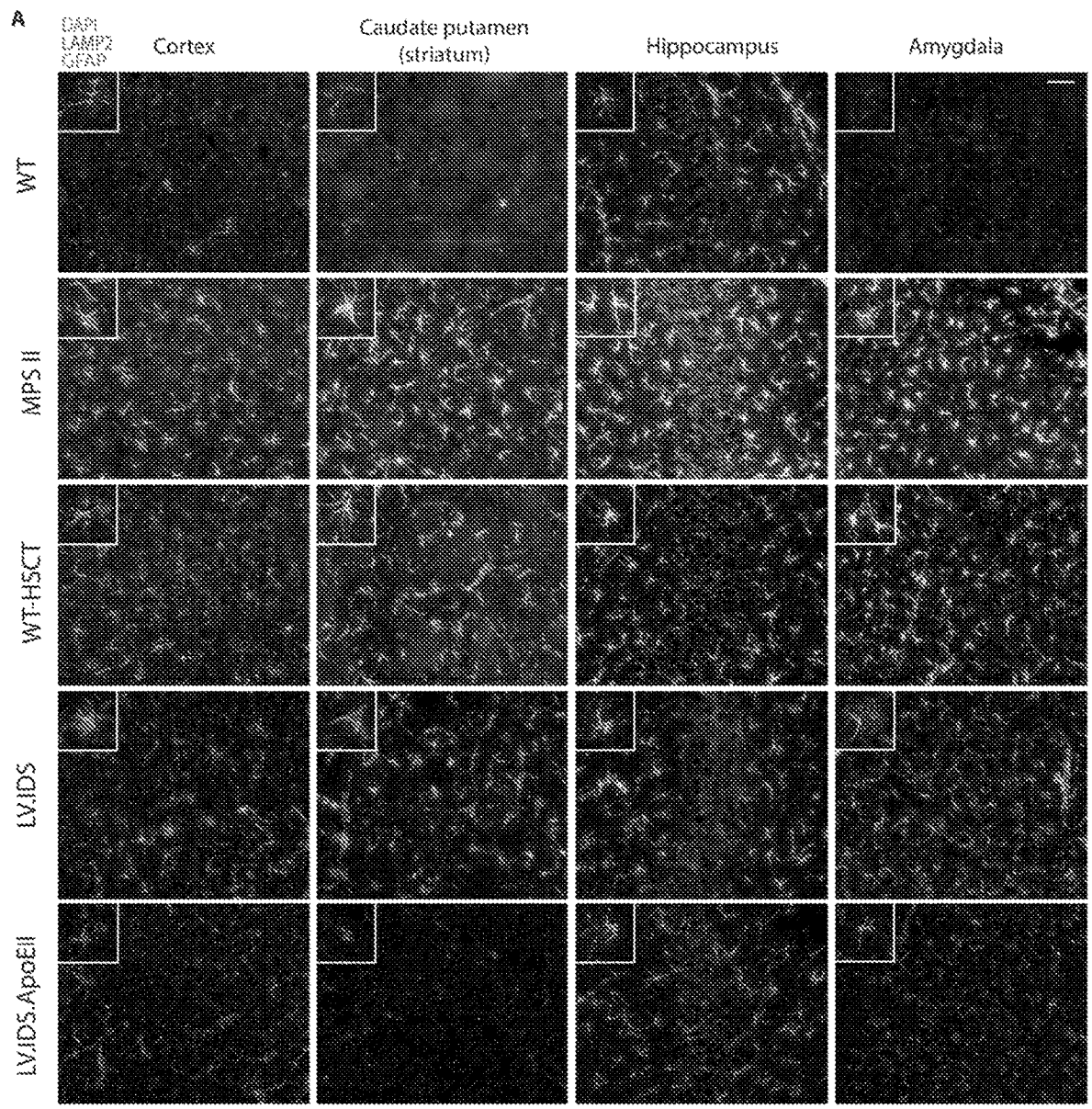
Figure 7:
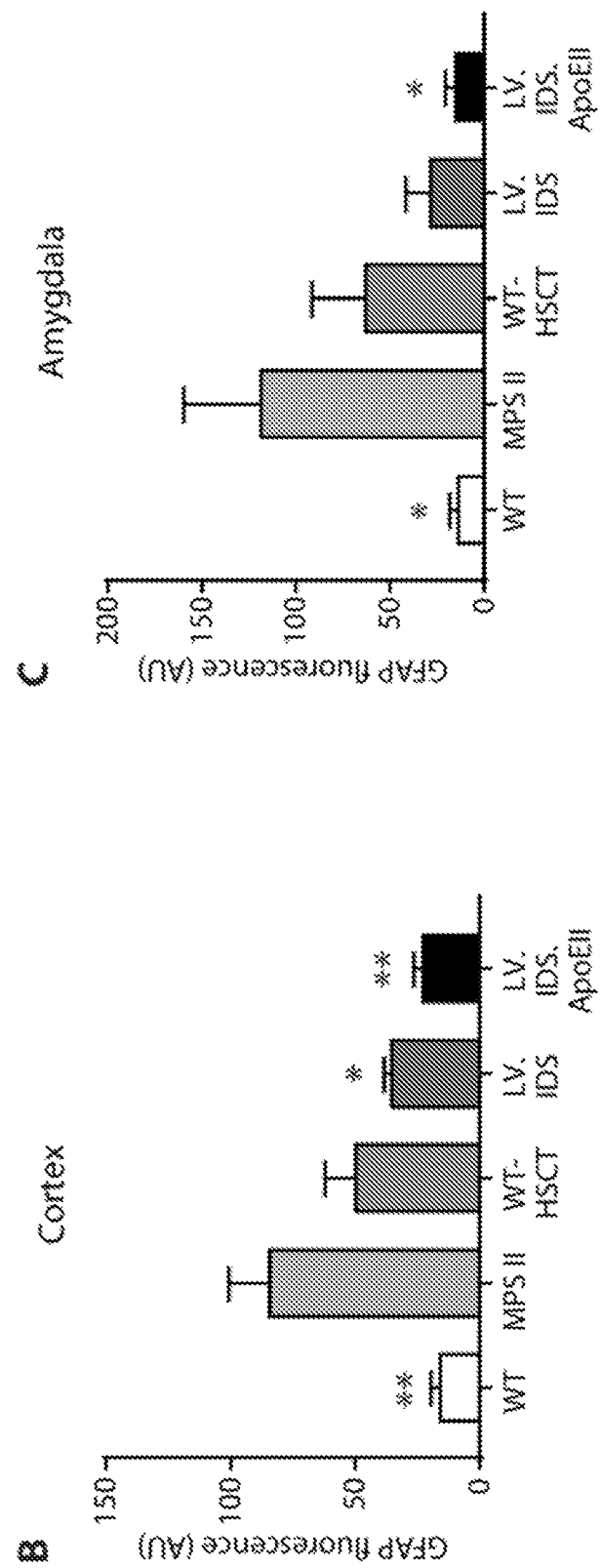
Figure 8:
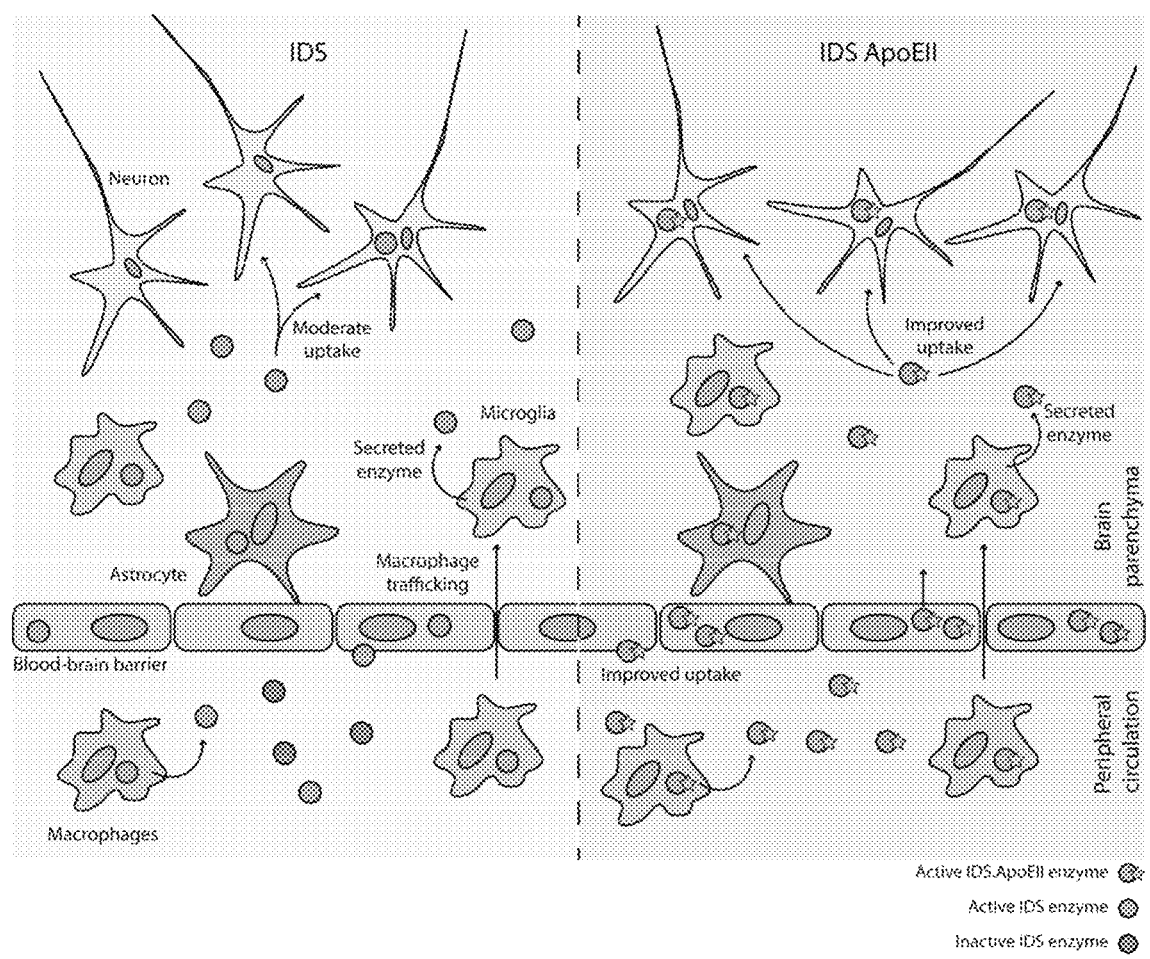
Figure 9:
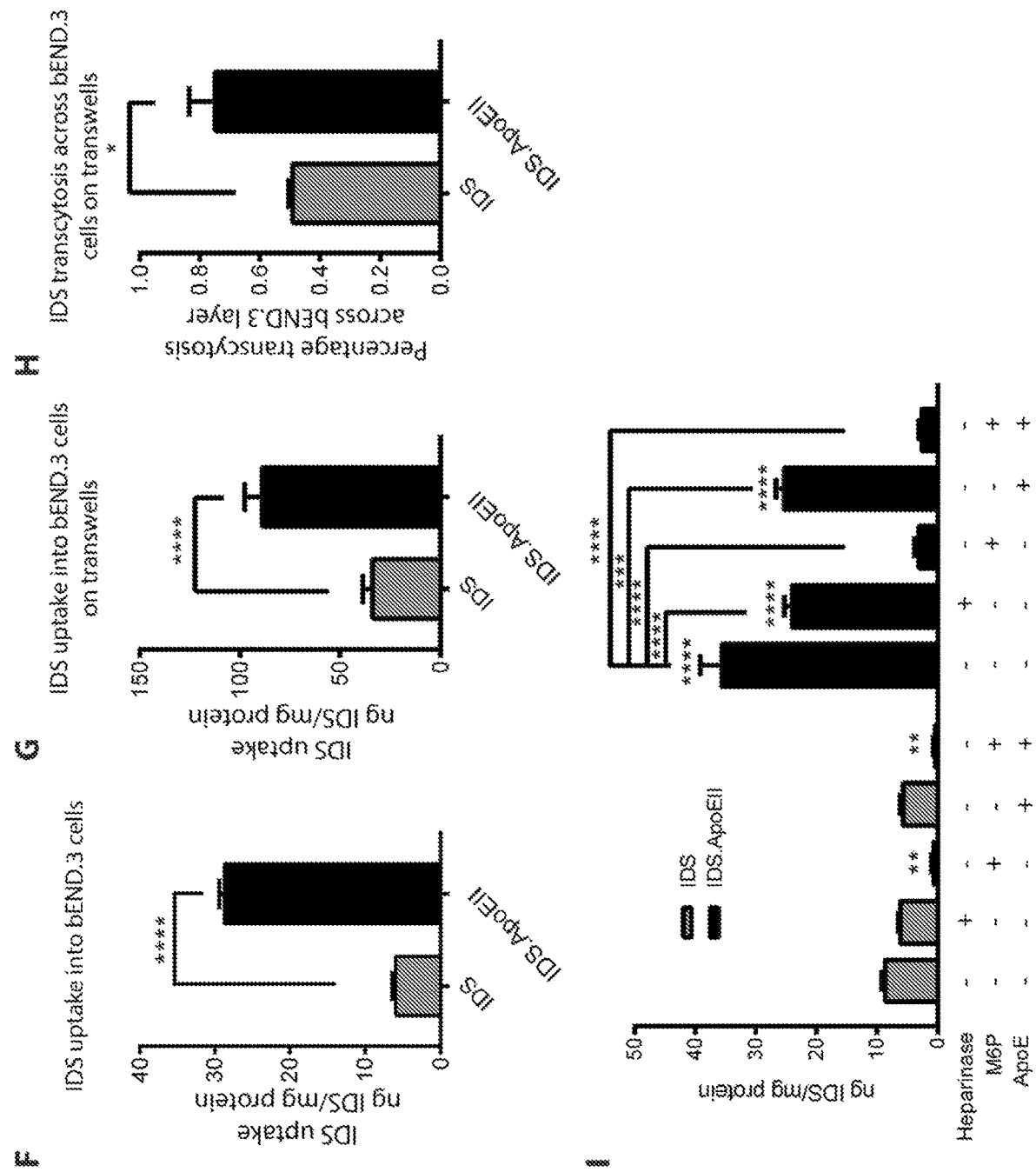

FIG. 1 shows the generation and validation of a novel blood-brain barrier-crossing IDS enzyme in vitro. (a) Schematic representation showing pCCL lentiviral vectors encoding for the codon-optimised human IDS gene, or the human IDS gene followed by a flexible linker and the ApoEII peptide sequence as a tandem repeat. Both lentiviral vectors are driven by the human CD11b promoter. (b) Schematic representation and sequences of the invariant linker and ApoEII tandem repeat added at the C-terminal of the IDS gene. (c) Graphs showing intracellular IDS enzyme activity measured in a human microglial cell line (CHME3) after transfection with 2 µg plasmid DNA of either LV.IDS or LV.IDS.ApoEII for 24 hours, and measured 48 hours post-transfection. n=3. (d) Secreted IDS enzyme activity measured in transfected human microglial cells (CHME3) with 2 µg plasmid DNA of either LV.IDS or LV.IDS.ApoEII for 24 hours, and measured 48 hours post-transfection. n=3one-way ANOVA, **=p<0.01 vs. non-transfected. (E) Uptake of IDS or IDS.ApoEII from media into bEND.3 cells after 24 hours, n=3 wells/condition (F) Receptor-mediated uptake of IDS or IDS.ApoEII through M6PR or LDLR 24 hours after blocking with 7.5 mM M6P or 50 µg/ml human recombinant apoE for 4 hours, n=3 wells/condition. Data are shown as mean±SEM, two-way ANOVA, *=p<0.05, =p<0.01, **=p<0.0001 comparisons are indicated by brackets;

FIG. 2 shows that LV.IDS and LV.IDS.ApoEII improve brain-specific IDS activity and express supra-physiological levels of active IDS in peripheral organs. (a) Schematic representation of the stem cell gene therapy strategy. Busulfan-conditioned 6-8-week-old MPS II mice were transplanted with $4 \times 10^5$ lin-HSCs transduced with LV.IDS or LV.IDS.ApoEII at an MOI of 100, or $1 \times 10^7$ total bone marrow cells. (b) Graph showing vector copy number and (c) Graph showing IDS enzyme activity were measured in transduced HSCs from colony-forming unit assays at transplant. (d) Graph showing donor chimerism in WBCs was measured by flow cytometry at 4-weeks post-transplant in all transplanted mice. (e) Graph showing vector copy number and (f) Graph showing IDS enzyme activity were measured in organs taken at 8 months of age, including BM, WBC/plasma, spleen and brain, from control and treated mice (n=6). (g) Graph showing VCN to enzyme activity correlation in individual mice in bone marrow, WBC/plasma, spleen and brain (n=6). (I) Graph showing IDS enzyme activity were measured in heart from control taken at 8 months of age. (j) Plasma clearance rate of IDS or IDSApoEII following injection into WT mice. (M) Correlation between plasma IDS enzyme activity and IDS protein measured by ELISA. Levels of lysosomal enzyme β-hexosaminidase activity were analysed in the (N) plasma, (O) spleen and (P) brain of 8-months old mice. Data are shown as mean±SEM, one way-ANOVA, *=p<0.05, =p<0.01, *=p<0.001, ****=p<0.0001 vs. MPSII, other comparisons are indicated by brackets;

FIG. 3 shows LV.IDS.ApoEII correct cognitive abnormalities in MPS II mice, and all transplants ameliorate coordination and balance. (a) Schematic representation of the Y-maze test. Mice are placed in the centre and allowed to explore freely for 10 minutes. (b) Graph showing spontaneous alternation in the Y-maze was measured in control and treated mice at 8 months of age, and (c) Graph showing the total number of entries was recorded as a proxy measure of locomotor activity. (d) Representation of the accelerating rotarod. (e) Graph showing 8-months-old control and treated mice were trialed 3 times on the accelerating rotarod for a maximum of 300 seconds (4-4 rpm over 300 seconds);

FIG. 4 shows LV.IDS.ApoEII normalises cytokines associated with neuro-inflammation in 8-months-old mice. (a)-(c) Graphs showing cytokine bead arrays measuring MIP-1α, MCP-1, IL-1α and RANTES were performed on whole brain lysate of 8-months-old mice using flow cytometry (n=6). (d) Graph showing MCP-1(CCL2). (e) Graphs showing total relative amounts of total HS. (f) compositional disaccharide analysis of HS from control and treated mice (n=6) analysed from brain samples. (g) Representative images of 30 µm sections of the motor cortex (M2) and striatum stained with isolectin B4 (ILB4) to identify activated microglia, 40×. Four 30 µm sections per mouse of the (h) cortex and (i) striatum were counted for the number of ILB4-positive cells (from approx. 0.26 mm to −1.94 mm from bregma), n=3/group. Scale bar: 50 µm. Data are shown as mean±SEM, one-way ANOVA, *=p<0.05, =p<0.01, *=p<0.001, ****=p<0.001 vs. MPSII, other comparisons are indicated by brackets;

FIG. 5 shows WT-HSCT, LV.IDS and LV.IDS.ApoEII normalise gross skeletal abnormalities in MPS II mice. (a) X-ray images of control and treated MPS II mouse craniums at 8 months of age. (b) Graph showing Zygomatic arch widths (c) Graph showing humerus widths. (d) Graph showing femur widths were analysed using ImageJ software (n=5-11); Cytokine bead arrays measuring (E) MCP-1, (F) MIP-1α and (G) RANTES and were performed on liver lysates of 8-months-old mice using flow cytometry, n=4-6. Gene expression of (H) Nppb and (I) Myh7 in hearts of control and treated MPS II animals (WT n=3, MPS II n=4, WT-HSCT, LV.IDS and LV.IDS.ApoEII n=6). (J) IDS-specific IgG antibody titers were measured in plasma. (K) Total IgG antibodies against IDS were determined in plasma samples by ELISA (Pos. control n=1, neg. control n=6, LV.IDS/LV.IDS.ApoEII n=6). Data are shown as mean±SEM, one-way ANOVA, *=p<0.05, =p<0.01, *=p<0.001, ****=p<0.0001 vs. MPSII;

FIG. 6 shows primary accumulation of heparan sulfate and its sulphation patterning in the brain is entirely normalized to WT levels using LV.IDS.ApoEII, not LV.IDS. (A) Total relative amounts of HS and (B) compositional disaccharide analysis of HS from control and treated mice were analysed from brain samples, n=6/group. (C) Representative images of 30 µm brains sections of the motor cortex (M2), caudate putamen (both approx. −0.46 mm from bregma), hippocampus (CA3) and amygdala (both approx. −1.22 mm from bregma) from control and treated mice stained with NeuN (neuronal nuclei; green) and LAMP2 (lysosomal compartment; red), n=6/group, 40×, nonlinear adjustments were made equally in all images to reduce background; gamma 0.72, input levels 0-190. Scale bar: 50 µm. Data are shown as mean±SEM, one-way ANOVA, *=p<0.05, =p<0.01,*=p<0.001, ****=p<0.0001 vs. MPSII, other comparisons are indicated by brackets;

FIG. 7 shows LV.IDS.ApoEII normalizes astrogliosis in 8-months-old MPS II mice. (A) Representative images of 30 µm brains sections of the motor cortex (M2, approx. −0.46 mm from bregma), caudate putamen (approx. −0.46 mm from bregma), hippocampus (CA3) and amygdala (both approx. −1.22 mm from bregma) from control and treated mice stained with GFAP (glial fibrillary acidic protein; green) and LAMP2 (lysosomal compartment; red), n=6/group, 40×, nonlinear adjustments were made equally in all images to reduce background; gamma 0.72, input levels 0-190. Scale bar: 50 µm. GFAP immunofluorescence was quantified in the (B) cortex and (C) amygdala of 8-months-old MPS II mice, n=3/group, AU: arbitrary units. Data are shown as mean±SEM, one-way ANOVA, *=p<0.05, **=p<0.01 vs. MPSII, other comparisons are indicated by brackets;

FIG. 8 shows a schematic diagram illustrating the proposed mechanism of action of the IDS.ApoEII enzyme in MPS II mice that allows IDS.ApoEII to correct the cognitive phenotype in MPS II mice. The ApoEII residue allows IDS to remain active for longer in plasma, leading to longer circulation time and higher chances of crossing into the CNS, whilst unmodified IDS is quickly degraded to an inactive form. Within the brain, corrected microglia derived from the bone marrow secrete IDS or IDS.ApoEII in similar levels but IDS.ApoEII uptake is more efficient and couple with improved stability, leads to better correction of primary storage and neuro-inflammation; and FIG. 9 shows graphs and immunofluorescent staining images showing increased plasma stability and enhanced uptake by brain endothelial cells via multiple mechanisms. (A) Plasma clearance of IDS protein measured in MPS II mice injected with 12 ng of total IDS enzyme at 1, 10 and 30 minutes post-injection, n=2/group. (B) Correlation between plasma IDS enzyme activity and IDS protein measured by ELISA. (C) FITC-dextran uptake into bEND.3 cells. (D, E) Immunofluorescent staining for LDLR (D) or LRP1 (E) in bEND.3 cells. (F) Uptake of IDS or IDS.ApoEII produced by CHME3 cells added to growth media of bEND.3 cells grown in monolayer culture for 24 hours. n=2 independent experiments, with 3 wells/condition. (G) Uptake of IDS or IDS.ApoEII produced by CHME3 cells added to growth media of bEND.3 cells grown in transwell culture for 24 hours. n=3 independent experiments, with 2 wells/condition. (H) Percentage transcytosis to the basal layer of bEND.3 cells from G. (I) Receptor-mediated uptake of IDS or IDS.ApoEII after 24 hours, following heparinase treatment of the cell layer or blocking with 7.5 mM M6P or 50 µg/ml human recombinant ApoE for 1 hour prior to enzyme addition. n=3 wells/condition. Data are mean±SEM, one-way ANOVA or T-test as appropriate, *=$p<0.05$, =$p<0.01$, *=$p<0.001$, ****=$p<0.0001$ vs. MPS II.

EXAMPLE 1

Experiments were conducted to transduce a vector containing a codon optimised IDS with haematopoietic stem and progenitor cells (HSPCs) which were subsequently tested in a mouse model for the expression of IDS and in particular to assess the amount of IDS passing through the blood brain barrier.

Expression Vectors

Human IDS cDNA (SEQ ID No. 2) was adapted so as to form codon-optimised IDS cDNA (coIDS) (SEQ ID No. 1) and synthesised using GeneArt technology (ThermoFisher, Paisley, UK) and cloned into the third-generation LV pCCL.sin.cPPT.hCD11b.ccdB.wpre using Gateway cloning to create pCCL.sin.cPPT.hCD11b.IDS.wpre). An additional vector containing the cDNA sequence (SEQ ID No. 3) of the brain-targeting peptide sequence ApoEII as a tandem repeat (LRKLRKRLLLRKLRKRLL) (SEQ ID No. 7) was inserted downstream of the codon-optimised human IDS cDNA using the long invariant linker cDNA sequence (SEQ ID No. 4) so as to provide a LGGGGSGGGGSGGGGSGGGGS linker (SEQ ID No. 8) (32). Plasmids were codon-optimised and synthesised using GeneArt technology and cloned as previously described into a 3$^{rd}$-generation lentiviral backbone. The amino acid sequence for human IDS cDNA (SEQ ID No. 2) is referenced as SEQ ID No. 6, wherein the amino acid sequence for coIDS cDNA (SEQ ID No. 1) is referenced as SEQ ID No. 5. The resultant amino acid sequences for both human IDS cDNA and coIDS cDNA are the same.

Transfection and Cross-Correction

Human microglial cells (CHME3) were transfected with 2 µg of plasmid CD11b.IDS or CD11b.IDS.ApoEII DNA using 7.5 mM high-potency linear polyethylenimine (pH 7.4, MW 40,000, Polysciences Inc., Warrington, Pa., USA) and 150 mM NaCl. Cells were collected 48 hours post-transfection in RIPA buffer (150 mM NaCl, 1% Triton-X100, 0.5% sodium deoxycholate, 0.1% SDS, 50 mM Tris, pH 8) and incubated on a shaker at 4° C. for 30 min, followed by centrifugation at 14,000 rpm, 4° C. for 20 minutes. Cell lysates were collected and stored at −80° C. Media supernatants were collected 48 hours post-transfection and centrifuged at 1,000 rpm, 4° C. for 10 minutes to remove cell debris and stored at −80° C.

LV Production and Titration

LV was produced (25) by transient transfection of HEK 293T cells with pMD2G, pΔ8.91gag/pol, LV plasmid (24, 25, 34, 35) and 7.5 mM polyethylenimine (40 kDa, Polysciences, Warrington, Pa., USA) (36). Lentiviral vector particles were concentrated by centrifugation at 21,191 g for 150 minutes at 4° C., resuspended in formulation buffer (PBS, 1 mg/ml human serum albumin, 5 µg/ml protamine sulphate, 40 mg/ml lactose, pH 7.2). EL4 mouse lymphoma cells (ATCC TIB-39; ATCC, Manassas, Va., USA) were transduced with three dilutions of concentrated LV and collected 72 hours later. Genomic DNA was extracted using GenElute Mammalian Genomic DNA Miniprep kit (Sigma-Aldrich, Poole, UK). The number of integrated viral genomes per cell was determined by quantitative PCR using a standard curve generated by dilutions of genomic DNA from an EL4 cell line clone containing 2 copies 2 integrated copies/cell of pHRsin.SFFV.eGFP.att.wpre (ALS EL4 eGFP 2.2) (24). A primer and probe set against wpre (TAMRA) were used as previously described (24, 25) and standardised against rodent gapdh (VIC) (Applied Biosystems, Paisley, UK).

Mice and Transplant Procedures

Female heterozygous for the X-linked allele were obtained from Prof. Joseph Muenzer (University of North Carolina at Chapel Hill, N.C., USA) and bred with wild-type C57BL/6J males (Envigo, Alconbury, UK) to obtain wild-type males and females, and affected hemizygous males and carrier females. MPSII were backcrossed onto the PEP3 CD45.1 congenic background (B6.SJL-Ptprc$^a$Pepc$^b$/BoyJ) to distinguish donor and recipient cells as previously described (24). WT littermates were used as controls throughout.

Total bone marrow mononuclear cells from MPSII mice were isolated from femurs and tibias, and lineage depleted using the murine lineage cell depletion kit (Miltenyi Biotec, Bisley, UK) according to the manufacturer's instructions. Cells were resuspended at 1×10$^6$ cells/ml in X-Vivo-10 media (BioWhittaker) containing 2% bovine serum albumin and stimulated using 100 ng/ml murine stem cell factor, 100 ng/ml murine fms-like tyrosine kinase-3 and 10 ng/ml recombinant murine interleukin-3 (Peprotech, Rocky Hill, N.J., USA) for 3 hours prior to transduction with a lentiviral vector for 20-24 hours at a multiplicity of infection of 100.

Six-to-eight-week-old mice housed in individually ventilated cages were myeloablated using 125 mg/kg Busulfan (Busilvex; Pierre Fabre, Castres, France) in five daily doses (25 mg/kg/day) via intraperitoneal injection. Prior to myeloablation, mice received acidified water (pH 2.8), irradiated food and mash. Within 24 hours of receiving the last injection of busulfan, mice were injected with 3-4×10$^5$ lineage-depleted transduced haematopoietic stem cells through the lateral tail vein. For wild-type transplants (WT-HSCT), mice received 1-2×10$^7$ untransduced total bone marrow cells.

Chimerism Analysis Using Flow Cytometry

Engraftment of donor haematopoietic stem cells was assessed at 4 weeks post-transplant in peripheral blood. Cells were stained with anti-mouse CD45.1-PE (donor HSCs), CD45.2-FITC (recipient HSCs), CD3-Pe-Cy5 (T-cell), CD19-APC-Cy7 (B-cell) and CD11b-Pe-Cy7 (macrophage/microglia) (BD Pharmingen, Oxford, UK) in a 5% solution of ToPro3 Iodide (ThermoFisher Scientific, Paisley, UK) and analysed on a BD FACS Canto II flow cytometer (BD).

Sample Processing

At 8 months of age, mice were anesthetized and transcardially perfused with 37° C. phosphate buffered saline to remove blood from organs. One brain hemisphere was fixed in 4% paraformaldehyde for 24 hours, transferred to a 30% sucrose, 2 mmol/l MgCl2/phosphate-buffered saline solution for 48 hours before freezing at −80° C. Pieces of brain, spleen, heart, kidney, muscle and liver were snap-frozen on dry ice and stored at −80° C. For IDS enzyme activity assays, samples were homogenised and sonicated in homogenisation buffer (0.5 mol/l NaCl, 0.02 mol/l Tris, 0.1% Triton-X100, pH 7-7.5) before centrifugation at 14,000 rpm at 4° C. for 30 minutes. Bone marrow samples were collected by flushing one tibia and femur with 1 ml 2% FBS/PBS, filtered using a 70 μm filter and lysed using red blood cell lysis buffer (150 mM NH4Cl, 10 mM KHCO3, 0.1 mM EDTA, pH 7.2-7.4). Supernatant was collected and stored at −80° C. Genomic DNA used for organ VCN analysis was extracted using GenElute Mammalian Genomic DNA Miniprep kit.

IDS Enzyme Activity

IDS enzyme activity was measured in a two-step protocol using the fluorescent substrate MU-aldoA-2S (Carbosynth, Compton, UK) and laronidase (Aldurazyme, Genzyme) as the second step substrate as previously described (37). The amount of starting material was standardised to 20 μg of total protein for plasma, 40 μg for liver, spleen and bone marrow, and 60 μg for brain using a BCA assay (ThermoFisher).

Preparation of Purified Glycosaminoglycans

Soluble brain fractions were collected and processed as previously described (38). Briefly, brain tissue was homogenised mechanically and Pronase-treated (1 mg/tissue) in 3 ml PBS for 4 hours at 37° C. 30 μl of TritonX100 was added to each sample for a 1% final concentration and incubated for an hour at room temperature prior to a second addition of 1 mg of Pronase for 4 hours at 37° C. Samples were loaded onto a pre-equilibrated DEAE-Sephacel column and hyaluronan was removed by washing the column with 50 ml of 0.25M NaCl/20 mM NaH$_2$PO$_4$·H$_2$O (pH 7). GAGs were eluted with 5 ml 1.5M NaCl/20 mM NaH$_2$PO$_4$·H$_2$O (pH 7), desalted using a PD10 column (Amersham, GE Healthcare) and freeze-fried.

Heparinase Digestions of HS and DS Followed by AMAC-Labelled Analysis

HS chains were digested using 5 mIU each of heparinase I, II and III (Seikagaku, Tokyo, Japan) in 100 μl of 0.1M sodium acetate and 0.1M calcium acetate (pH 7). Resulting disaccharides were freeze-dried, re-dissolved in 20 μl of 0.1 M 2-aminoacridone (AMAC) in 85% Me$_2$SO/15% acetic acid (v/v) and incubated at room temperature for 20 minutes. 20 μl of NaBH$_3$CN was added to each sample and incubated overnight at room temperature. AMAC-labelled disaccharides were separated by reverse phase high-performance liquid chromatography using a Zorbax Eclipse XDB-C18 column (2.1×500 mm, 3.5 μm) (Agilent Technologies, Stockport, UK).

Cytometric Bead Array (CBA)

Levels of IL-1α, MCP-1, MIP-1α and RANTES were measured in whole brain extracts at 8 months of age (n=6/group) using BD Cytometric Bead Array (CBA) Flex Set kits (BD Biosciences, Oxford, UK) (40). Analysis was performed on a FACS Canto II flow cytometer (BD). Identification of the singlet bead population was performed using the FSC vs SSC plot, and each individual cytokine bead was separated using APC and APC-Cy7, with cytokine levels measured using PE. The results were exported and analysed using FCAP Array software (BD). Brain protein concentrations were obtained using the BCA assay and cytokine levels were standardised to protein level for each sample.

Behavioural Analysis

Rotarod

The rotarod test was used to evaluate motor coordination and balance at 32 weeks of age as previously described with minor modifications (41). Male mice (WT, n=16, MUT, n=12, treatment groups n=12-16) were trained on the rotarod (Ugo Basile, Varese, Italy) across three training trials (4 rpm for 120 seconds; 4 rpm for 300 seconds; 4-40 rpm over 300 seconds) with a 30 minute interval between each session. Three test trials were carried out 24 hours post-training. For test trials, the rotarod rotated at an accelerating speed of 4 to 40 rpm over 300 seconds, with a 5 minute rest between each trial. Latency to fall was recorded for all training and test trials, and latency to fall off was calculated as percentage of total trial time.

Spontaneous Alternation

Spatial working memory was assessed in all mice at 32 weeks of age using the spontaneous alternation test (41, 42). Spontaneous alternation was assessed in a single 10-min trial in a Y-maze consisting of three identical arms. The test mouse was placed in the middle of the three arms and allowed to explore freely. Spontaneous alternation was described as successive entries into three arms, in overlapping triplet sets. The effect was calculated as percent alternation=[no. of alternations/(total number of arm entries−2)]×100.

X-Ray Imaging of Live Mice

Control and treated mice were anesthetised using isoflurane and radiographed (45 keV) using the Bruker InVivo Xtreme system fitted with a high sensitivity, back-thinned back-illuminated 4MP, 16-bit, digital CCD camera. X-ray images were analysed using ImageJ software for individual bones widths.

Statistics

Statistical analysis was performed using GraphPad Prism 7 software (La Jolla, Calif., USA). Two-tailed parametric unpaired t-tests were applied for individual group comparisons with significance set at p<0.05. One-way ANOVAs were performed for multi-group analysis followed by Tukey's multi-comparisons test.

Development and In Vitro Validation of Blood-Brain Barrier-Targeting IDS Enzyme

During the experiments, the inventors sought to develop a novel MPS II-specific sulphatase enzyme that was able to efficiently cross the BBB through the use of the LDLR via receptor-mediated transcytosis. Novel lentiviral vectors encoding for human IDS alone, or human IDS linked to the human ApoE receptor-binding region as a tandem repeat, were constructed under the human myeloid-specific CD11b promoter (as illustrated in FIG. 1a).

This sulphatase was modified by adding an invariant flexible linker to the C-terminal of the IDS gene, followed by the codon-optimised sequence of the receptor-binding portion of human ApoE as a tandem repeat (as illustrated in FIG. 1b). Typically, the addition of a linker and peptide can alter protein folding and detrimentally affect enzyme activity.

To verify that the inventive construct still allowed for IDS overexpression and secretion, a human microglial cell line (CHME3) was transfected with plasmid DNA expressing either LV.IDS or LV.IDS.ApoEII. 26-fold and 24-fold increases in cellular activity were observed with LV.IDS and LV.IDS.ApoEII, respectively (as shown in FIG. 1c). More importantly, increases of 84-fold and 81-fold in secreted IDS activity were detected 72 hours post-transfection (FIG. 1d). Notably, this demonstrates that the C-terminal modifications do not negatively impact secretion or expression of the modified IDS enzyme in vitro. A significantly increased uptake of IDS.ApoEII over IDS in mouse endothelial bEND.3 cells after 24 hours (FIG. 1E, 1F) was detected, predominantly, but not exclusively, via M6P receptors (FIG. 1F)

LV.IDS- and LV.IDS.ApoEII-Mediated Stem Cell Gene Therapy Improve IDS Enzyme Activity in the Brain and Express Supra-Physiological Levels of Active IDS in Peripheral Organs $4 \times 10^5$ lineage-depleted haematopoietic stem cells (HSCs) were transplanted from MPS II donors transduced with either LV.IDS or LV.IDS.ApoEII, expressing IDS or IDS.ApoEII, into 16 busulfan-conditioned 6-8 week-old MPS II mouse recipients (as illustrated in FIG. 2a). Unmodified total bone marrow cells were also injected into fully myeloablated MPS II recipients, equivalent to an allogeneic stem cell transplant, and are henceforth referred to as WT-HSCT.

IDS activity and vector copy number (VCN) were measured in lineage-depleted HSCs (lin-HSCs) isolated from colony-forming unit (CFU) assays prior to transplant. The experiments demonstrated mean vector copy numbers of 3.1 and 3.8 in the LV.IDS- and LV.IDS.ApoEII-transduced HSCs (as shown in FIG. 2b) and overexpression of IDS enzyme by 124-fold and 152-fold over WT, respectively (as shown in FIG. 2c). These data demonstrate a positive correlation between the number of vector genome integrations and enzyme overexpression in haematopoietic cells. Flow cytometry analysis of peripheral WBCs at 4-weeks post-transplant demonstrated full engraftment of transduced cells into MPS II recipients, achieving between 80-100% of donor CD45.1+ cells (as shown in FIG. 2d).

To assess therapeutic efficacy of this novel gene therapy in MPS II, 6 animals from each group were sacrificed at 8 months of age for biochemical analysis of central and peripheral organs. Vector integrations were detected in total BM, WBCs, spleen and brain, with a significantly lower mean in LV.IDS.ApoEII-treated mice in WBCs only (as shown in FIG. 2e). A small number of animals consistently showed lower VCNs in all organs assessed, but received modified HSCs in separate transplantation procedures. Supra-physiological levels of IDS were observed in BM, plasma and spleen for both LV.IDS- and LV.IDS.ApoEII-treated groups. IDS enzyme activity levels in the brain were also elevated compared to untreated MPS II animals, and are equivalent to between 1.5% and 8% of normal IDS activity in WT brains. The WT-HSCT transplants restored IDS levels equivalent to WT in BM, plasma and spleen only, whilst no noticeable increase in IDS activity was detected in the brain over untreated MPS II animals.

Advantageously, IDS activity in plasma of LV.IDS.ApoEII-treated animals was 3-fold higher than in the LV.IDS-treated group, suggesting potential alterations in enzyme stability and circulation time, secretion or uptake into cells (as shown in FIG. 2f). Furthermore, positive correlations between VCN and IDS enzyme activity levels further suggests that enzyme overexpression is driven by increases in genome integration of the IDS gene (FIG. 2g). However, correlations between WBC VCN and IDS activity in plasma show significant differences between LV.IDS and LV.IDS.ApoEII groups, where low VCN in LV.IDS.ApoEII WBCs results in IDS levels that are higher than in any of the LV.IDS-treated mice, suggesting mechanistic differences in enzyme production, uptake or secretion. Additionally, higher IDS levels in plasma of LV.IDS.ApoEII-treated animals does not yield higher IDS enzyme levels in brain, as enzyme levels in the brain are equivalent in both LV-treated groups (as shown in FIG. 2f). The clearance rate of injected enzyme in plasma was similar between the IDS and IDS.ApoEII groups (FIG. 2J). Positive correlations between VCN and IDS enzyme activity levels in BM, spleen, brain, lung, liver and heart, was observed with nearly equivalent activity/ VON for both IDS and IDS.ApoEII, suggesting that enzyme overexpression is driven by increases in genome integration of the IDS gene (FIG. 2K).

A value of 15.41 units/VON of enzyme activity was detected in LV.IDS.ApoEII compared to 2.56 units/VON in LV.IDS in plasma, suggesting that IDS enzyme activity in plasma is significantly increased by fusion of the ApoEII residue. This increase in enzyme activity in IDS.ApoEII is further demonstrated by comparing IDS enzyme activity to IDS protein in plasma, where IDS.ApoEII appears to be more active per unit of IDS protein (FIG. 2M).

Lysosomal Homeostasis

The dysfunction and uncontrolled accumulation of primary storage material in lysosomes in MPS II is likely to have a profound impact on lysosomal regulation and subsequent homeostasis. Importantly, neurodegeneration is associated with lysosomal dysfunction and impaired autophagy. In disease states such as MPS II, endogenous lysosomal enzymes can compensate for the deficiency of another lysosomal enzyme. Elevated levels of the lysosomal hydrolase β-hexosaminidase were detected in the plasma (2-fold over WT), spleen (1.53-fold over WT) and brain (2-fold over WT) of untreated MPS II animals (FIG. 2N-P). Plasma, spleen and brain levels of β-hexosaminidase were fully normalized back to WT levels in both LV.IDS- and LV.IDS.ApoEII-treated groups (FIG. 2N-P). WT-HSCT normalized β-hexosaminidase levels in plasma and spleen (FIG. 2N, 2O), and ameliorated levels in the brain without achieving complete normalization to WT levels (FIG. 2P).

Heparan Sulfate Accumulation is Fully Normalized with LV.IDS.ApoEII but not LV.IDS HS and CS/DS glycosaminoglycans were purified from brain samples, and analysed and quantified by reverse-phase HPLC. A 6-fold increase in total HS was detected in brains of MPS II mice and mice treated with WT-HSCT (FIG. 6A). Mice treated with LV.IDS showed a decrease in total HS accumulation in the brain to approximately 3-fold of WT levels. Most importantly, LV.IDS.ApoEII-treated mice showed a complete normalization of brain HS levels back to WT levels and significantly lower levels of HS when compared to LV.IDS (FIG. 6A).

HS composition analysis in MPS II mice showed that 31.1% of brain HS consisted of the fully sulfated UA(2S)-GlcNS(6S), compared to 12.3% in control WT mice (FIG. 6B). In WT mice, these generally form clusters with other sulfated disaccharides along the chain, with significant increases in sulphation along the entirety of the HS chain in MPS II mice. This trend was reversed with WT-HSCT, LV.IDS and most effectively by LV.IDS.ApoEII. Similarly, increases in UA(2S)-GlcNS from 16.8% in WT mice to 31.1% in MPSII mice were observed, and fully corrected down to 18.4% in the LV.IDS.ApoEII group only.

It was also observed a significant reduction in total brain CS/DS levels in LV.IDS.ApoEII mice when compared to MPS II (Supplementary FIG. 2A); although no significant differences were detectable between WT and MPS II mice. increases in UA(2S)-GalNAc(4S) from 1.03% in WT mice to 6.5% in MPS II mice were detected, with complete correction obtained in the LV.IDS.ApoEII group.

LV.IDS.ApoEII Corrects Lysosomal Accumulation in Neurons Throughout the Brain

The effects of increased IDS enzyme levels in the brains of transplanted MPS II mice at 8 months of age (6 months post-transplant) on lysosomal enlargement and substrate accumulation in neurons (NeuN) using the lysosomal marker LAM P2 were then determined. WT animals displayed weak, punctate and perinuclear LAMP2 staining that only partially co-localized with NeuN in the motor cortex (layer V/VI). Untreated MPS II and WT-HSCT-treated animals displayed strong co-localized staining of NeuN and LAM P2 in the motor cortex, caudate putamen, hippocampus and amygdala, suggesting a heavy lysosomal burden in neurons or satellite glial cells (FIG. 6C). LV.IDS mediated improvements in the cerebral cortex, caudate putamen and amygdala, with engorged lysosomal compartments in the hippocampus still visible, suggesting only a partial correction of primary substrate accumulation, which strongly correlates to the levels of HS detected in the brain (FIG. 6A, 6B). LV.IDS.ApoEII fully normalised the increased LAMP2 staining in the cortex, caudate putamen and hippocampus, and considerably reduced the amount of lysosomal burden in the amygdala (FIG. 6C).

LV.IDS.ApoEII Fully Normalizes Neuro-Inflammation Whilst LV.IDS Mediates an Improvement in MPS II Mice Astrocytes have been found to mediate a strong neuro-inflammatory response in MPS disorders, which translates into reactive gliosis, astrogliosis and increased levels of inflammatory cytokines. Brain coronal sections of control and treated MPS II mice were stained with the astrocytic marker GFAP (glial fibrillary associated protein; green) and LAMP2 (red). Significantly more GFAP staining was observed in untreated MPS II than in WT mice in the cortex, caudate putamen and amygdala, indicative of extensive astrogliosis (FIG. 7A). Additionally, strong co-localization of GFAP and LAMP2 was observed in the caudate putamen, hippocampus and amygdala in untreated and WT-HSCT mice (FIG. 7A), suggesting significant lysosomal substrate accumulation in astrocytes in addition to neurons (FIG. 6C). LV.IDS.ApoEII was able to fully abrogate astrogliosis and decrease LAMP2 staining back to WT levels in the cortex, caudate putamen, hippocampus and amygdala, correlating to decreases in substrate storage and inflammatory cytokines (FIG. 6A, 6B, 6A-D). Similarly, LV.IDS decreased the number of reactive astrocytes present in the cortex, caudate putamen and amygdala.

LV.IDS.ApoEII Fully Corrects Cognitive Abnormalities and Coordination and Balance in MPS II Mice To understand whether CNS and skeletal phenotype in the MPS II mouse model could be ameliorated with LV.IDS- or LV.IDS.ApoEII-modified HSCs, functional studies of cognition and sensorimotor performance were performed at 8 months of age, equivalent to 6 months post-transplant, on all treated animals in each group. Cognitive evaluation of spatial working memory was evaluated using the Y-maze test, which exploits their innate preference to explore novel arms over recently explored arms over 10 minutes (as illustrated in FIG. 3a).

Neurocognitive assessment showed complete normalisation of spontaneous alternation in LV.IDS.ApoEII-treated mice, but not in the LV.IDS-treated or WT-HSCT groups (FIG. 3b). This suggests not only complete correction of cognitive dysfunction seen in the MPS II mouse model using LV.IDS.ApoEII, but also shows the prevention of further cognitive deterioration associated with progressive MPS II disease. Interestingly, WT-HSCT has no positive impact on the cognitive symptoms associated with MPS II;

further highlighting that WT-HSCT may not be suitable to treat the brain in MPS II. The total number of entries into the different arms of the Y-maze can also be used as a proxy measure of overall activity. No differences in the number of total entries were detected between all tested groups, suggesting a real phenotypic rescue of cognitive symptoms in LV.IDS.ApoEII-treated animals (as shown in FIG. 3c).

Control and treated mice also underwent testing on the rotarod, a well-established test for sensorimotor coordination and balance in movement disorders in rodents (as shown in FIG. 3d). 8-months-old MPSII mice showed a reduction in performance on the accelerating rod as previously described. This was entirely rescued by all transplant treatments, including WT-HSCT (as shown in FIG. 3e).

Neuro-Inflammatory Cytokines are Normalised with LV.IDS.ApoEII but not LV.IDS

Cytometric bead arrays (CBA) were used to quantify a number of inflammatory cytokines associated with chronic neuro-inflammation from whole brain extracts of control and treated mice at 8 months of age. For the first time, we identified significant increases in macrophage inflammatory protein (MIP-1α/CCL3), interleukin 1α (IL-1α) protein, RANTES (CCL5) and monocyte chemoattractant protein (MCP-1/CCL2) in untreated MPS II animals (as shown in FIGS. 4a, 4b, 4c, 4d). MIP-1α, IL-1α and RANTES protein levels were normalised with LV.IDS.ApoEII, and only partially with LV.IDS, and MCP-1 levels remained elevated for all groups (as shown in FIG. 4b).

Additionally, we observed a 30-fold and 25-fold increase in isolectin B4 (ILB4)-positive cells in the cortex and striatum of untreated MPS II mice, respectively (FIG. 4E, 4F, 4G), suggesting extensive activation of microglia and subsequent neuro-inflammation. Interestingly, both WT-HSCT and LV.IDS reduced ILB4 staining to 14-fold and 12-fold of WT levels in the cortex (FIG. 4F), and to 15-fold and 13-fold of WT staining in the striatum (FIG. 4G), respectively. Most importantly, LV.IDS.ApoEII was able to completely normalize the number of activated microglia in both the cortex and striatum (FIG. 4F, 4G), which strongly correlates with the reduction of neuro-inflammation cytokines previously observed and the full abrogation of astrocytosis in LV.IDS.ApoEII.

Overall, this suggests that the release of neuro-inflammatory cytokines and chemokines, reactive astrogliosis and microglial activation in MPS II can be fully abrogated by LV.IDS.ApoEII, and only partially with LV.IDS.

Heparan Sulphate Accumulation is Fully Normalised with LV.IDS.ApoEII but not LV.IDS HS GAGs were purified from control and treated brains of MPS II mice and depolymerised into individual HS disaccharides using bacterial heparinase enzymes followed by fluorescent-tagging of reducing ends of individual disaccharides using AMAC. Reverse-phase HPLC separation was used to quantify and determine the individual contributions and sulphation patterns of each HS disaccharide.

HPLC analysis allows for the relative levels of total HS to be calculated between WT, untreated MPS II and all treatment groups (as shown in FIG. 4e). A 6-fold increase in total HS was detected in brains of MPS II mice and mice treated with WT-HSCT ($p<0.0001$). Interestingly, mice treated with LV.IDS showed a decrease in total HS accumulation in the brain to approximately 3-fold of WT levels. Most importantly, LV.IDS.ApoEII-treated mice showed a complete normalisation of brain HS levels back to WT levels (as shown in FIG. 4e).

HS composition analysis showed significant increases of tri-sulphated disaccharide UA(2S)-GlcNS(6S), and increases in UA(2S)-GlcNS in untreated MPS II brains (as shown in FIG. 4f). This trend was partially reversed with WT-HSCT and LV.IDS, although full correction back to WT levels was only obtained in the LV.IDS.ApoEII group.

Mono-sulphated HS disaccharides showed a significantly different trend; where untreated MPS II and WT-HSCT-treated levels of UA-GlcNS were lower than in WT brains (as shown in FIG. 4f). This was partially improved with the LV.IDS treatment, but only fully corrected in the LV.IDS.ApoEII group.

Skeletal Pathology is Ameliorated by all Transplant Strategies in MPS II Mice

Total body X-rays under full anaesthesia were performed on control and treated mice to obtain robust data on the extent of skeletal symptoms in the MPS II mouse model. Widths of zygomatic arches and appendicular long bones (humeri and femurs) were measured using ImageJ imaging software.

The width of the zygomatic arches, which are significantly increased in untreated MPS II animals, were reduced to WT dimensions in all transplanted groups, including WT-HSCT (as shown in FIGS. 5a, 5b). Humerus widths were significantly reduced in WT-HSCT and LV.IDS groups, although full correction was only obtained in the LV.IDS.ApoEII-treated animals (as shown in FIG. 5c). Moreover, femur widths in all treated animals showed no significant differences when compared to WT animals, suggesting significant skeletal rescue.

Peripheral Inflammation is Abrogated Following Transplantation of WT, LV.IDS- or LV.IDS.ApoEII-Modified HSCs Elevated levels of MCP-1, MIP-1α and RANTES were detected in the livers of MPS II mice at 8 months of age, which were completely abrogated by WT-HSCT, LV.IDS- or LV.IDS.ApoEII treatments (FIG. 5E-5G). These data suggest that WT-HSCT, LV.IDS and LV.IDS.ApoEII produce sufficient amounts of peripheral enzyme to fully correct chronic peripheral inflammation in MPS II mice.

Gene Expression of Heart Failure Markers Nppb and Myh7 are Normalized in WT-HSCT, LV.IDS and LV.IDS.ApoEII Groups The expression of Nppb and Myh7, two markers associated with cardiomyopathies and cardiac pathology, which could be indicators of higher risks of heart failure in the MPS II mouse model, were investigated. The expression of Nppb, which encodes for the brain natriuretic peptide (BNP) that is secreted from the ventricles and regulates myocyte stretching and blood pressure, was found to be approximately 16-fold higher in MPS II than in WT male mice (FIG. 5H). Nppb expression was fully stabilized back to WT levels in WT-HSCT, LV.IDS and LV.IDS.ApoEII groups (FIG. 5H). Myh7 expression, primarily found in embryonic heart and encodes for myosin heavy chain beta as a key component of cardiac muscle and type I muscle fibers, was elevated in untreated MPS 11 animals. Myh7 expression in WT-HSCT, LV.IDS and LV.IDS.ApoEII groups was similar to WT expression (FIG. 5I).

Overexpression of IDS Following Transplantation of LV.IDS and LV.IDS.ApoEII-Transduced HSCs does not Yield an Immune Response to Human IDS To study whether gene-modified cells were able to mediate tolerance to human IDS post-transplant, we analysed plasma from mice that received full myeloablative conditioning followed by either LV.IDS or LV.IDS.ApoEII transplant, both over-expressing human IDS, for IgG antibodies against human IDS. Overall IDS-specific IgG titers in LV.IDS and LV.IDS.ApoEII groups remained in the normal range and did not contribute to an immune response to the enzymes (FIG. 5J).

LV.IDS.ApoEII Treatment Acts Through Multiple Mechanisms

Following the observed increase in enzyme activity in plasma and the increased enzyme activity per VCN in LV.IDS.ApoEII-treated mice (FIG. 2f, 2j), we hypothesized that the circulation time of enzyme might be increased. Equivalent levels of IDS and IDS.ApoEII enzyme were injected into MPS II mice and protein levels monitored by ELISA (FIG. 9A). Interestingly, enzyme clearance rate, whether from degradation or uptake into organs, was similar between the IDS and IDS.ApoEII groups and was effectively cleared in both groups by 30 minutes.

Next levels of active enzyme in the plasma compared to total IDS protein were compared and measured by ELISA, hypothesizing that the conformation of the enzyme may be altered with the addition of the ApoEII residue, conferring additional protection against degradation. IDS.ApoEII appeared to be more active per unit of IDS protein in plasma (FIG. 9B). This may suggest the active site of native IDS enzyme is rapidly degraded in plasma whereas the ApoEII addition is protective, effectively prolonging enzyme activity in vivo.

The BBB endothelial cell line bEND.3 was used to determine whether there was any difference in enzyme uptake by endothelial cells. These cells produce an effective BBB layer in transwells (FIG. 9C) and express both LDLR and LDLR-related protein 1 (LRP1) receptors (FIG. 9D, 9E). In order to ensure that each enzyme has a similar M6P status to that of the HSCGT produced enzyme, we used IDS and IDS.ApoEII enzyme secreted into the media after transfection of CHME3 human microglial cells and standardized by ELISA. In monolayer culture, we compared the uptake of IDS versus IDS.ApoEII into bEND.3 cells, identifying a 4.7-fold increase in cellular uptake with the addition of the ApoEII peptide (FIG. 9F). The uptake and transcytosis of IDS or IDS.ApoEII across polarized cell layers of bEND.3 endothelial cells in transwells to mimic the BBB were then compared. 2.6-fold increases in uptake were apparent, similar to when cells were grown in monolayer, together with a 1.5-fold increase in transcytosis to the basolateral side of the transwell (FIG. 9G, 9H).

In addition, blockade of ApoE dependent receptors using ApoE or blockage of M6P receptors using M6P (FIG. 9I), revealed that IDS.ApoEII was preferentially and unexpectedly taken up via M6P receptors, although blockade with ApoE peptide also significantly inhibited uptake of IDS.ApoEII by approximately 30%. The ApoEII peptide sequence also codes for a HS site, required as a co-receptor for receptor/ligand binding of ApoE to its receptors, including LDLR and LRP1 (Ji et al, 1993). Heparinase pre-treatment of cells also resulted in a reduction in IDS.ApoEII uptake by approximately 30%, similar to results with ApoE peptide, suggesting that ApoE/HS may also be important in uptake and transcytosis across bEND3 cells.

Discussion

The addition of the linker and ApoEII peptide did not change the expression, production or secretion of the IDS enzyme in vitro, but produced supra-physiological levels of IDS enzyme in transduced HSCs using both LV.IDS and LV.IDS.ApoEII vectors for similar vector copy number. Complete engraftment of CD45.1+ donor cells (>80%) was obtained using full myelo-ablative conditioning using busulfan in all transplanted animals, with no significant differences in downstream in vitro differentiation assays at the time of transplant (data not shown).

Surprisingly, IDS enzyme activity levels in plasma in the LV.IDS.ApoEII group were approximately 3-fold higher than in LV.IDS, even with lower VCN in WBCs. This translates to higher enzyme activity per copy in the LV.IDS.ApoEII group, suggesting that the ApoEII residue stabilizes or improves activity by changing its conformation, and appear to provide a protective effect against enzyme inactivation, but not clearance in plasma (FIG. 8). A higher uptake of IDS.ApoEII in bEND.3 cells compared to unmodified IDS was detected and this was believed to be mediated predominantly by M6PR. The receptor-binding portion of apoE used in the IDS.ApoEII fusion enzyme (residues 142-147) is able to form a high affinity binding complex with an octasaccharide HS fragment composed of four repeats of UA(2S)-GlcNS(6S), which are abundant on endothelial cell surfaces and even more abundant in MPS II. HS typically acts as a co-receptor in many receptor ligand interactions and increased binding to HS proteoglycans (HSPG) through ApoEII could mediate an increase in cellular uptake through the LDLR, LDLR-related protein 1 (LRP1), M6P or by direct uptake of an apoE-HSPG complex.

Similar amounts of enzyme activity within the brain between the LV.IDS and LV.IDS.ApoEII groups were detected, but complete correction only in LV.IDS.ApoEII with improved clearance of LAM P2 from neurons and astrocytes. One explanation for this is that enzyme uptake from the interstitial space may be more efficient using IDS.ApoEII, thereby correcting resident brain cells much more effectively than unmodified IDS whilst maintaining the same overall levels (FIG. 8).

Full correction of primary storage elevations and a global normalisation of the sulphation patterning, which plays a major role in neuro-inflammation, were observed in LV.IDS.ApoEII-treated animals. Partial correction of the primary HS storage in the brain is insufficient to correct cognitive behavior. The accumulation of HS in MPS II likely could provide one of the first signals that trigger neuro-inflammation and exacerbate neurodegeneration. The sulphation patterning also plays a crucial role in cellular function and HS-binding homeostasis, as 6-O- and 2-O-sulphated HS are essential for signaling of fibroblast growth factor and stromal cell derived factor-1 (CXCL12). Indeed, abnormal excess HS in MPS I was shown to reduce migration of HSCs under limiting conditions via sequestration of CXCL12 (42). In the context of this study, increases in sulfated disaccharides in brain tissue of diseased animals could promote improved cellular uptake of the IDS.ApoEII enzyme, thereby enhancing enzyme targeting to diseased cells.

A significantly increased uptake of IDS.ApoEII in bEND.3 cells compared to IDS via both an ApoE/HS based mechanism and via M6P receptors was observed. The use of multiple targeting mechanisms could mediate more efficient targeting to enzyme-deficient cells throughout the body as well as across the BBB. The receptor-binding portion of ApoE used here is able to form a high affinity binding complex with an octasaccharide HS fragment composed of four repeats of UA(2S)-GlcNS(6S), which are abundant on endothelial cell surfaces and even more abundant in MPS II. In the context of this study, increases in sulfated disaccharides in brain tissue of diseased animals could promote improved cellular uptake of the IDS.ApoEII enzyme, via the HS binding motif in the ApoEII peptide, thereby enhancing enzyme targeting to diseased cells. HS typically acts as a co-receptor in many receptor ligand interactions and increased binding to HS proteoglycans through ApoEII could mediate an increase in cellular uptake through the LDLR, LRP1, M6P or by direct uptake of an ApoE-HSPG complex. Improved plasma stability coupled with increased BBB uptake and transcytosis could together account for the normalization of HS and DS storage, as well as several other neuropathologies in the brain seen with LV.IDS.ApoEII, in the absence of significant differences in brain enzyme amount. A similar effect of increased uptake, clearance and cell association for similar enzyme activities have been seen in MPS IIIB and Pompe disease using enzymes coupled to GILT tags targeting an alternative epitope of M6P via an IGFII receptor directed peptide. In this study small increases in brain enzyme activity with SGSH.ApoB was shown with no significant changes over native IDS.

Neuro-inflammation is commonly reported in LSDs, likely caused by the accumulation of various undegraded molecules, which cooperatively activate and perpetuate a neuro-inflammatory milieu that may exacerbate the disease itself. MPS II mice elicit a strong inflammatory response in the brain, with elevated levels of MIP-1α, IL-1α, RANTES and MCP-1. MIP-1α, IL-1α and RANTES levels were fully normalised in the LV.IDS.ApoEII group, with only partial decreases in LV.IDS-treated mice. Interestingly, MCP-1 levels remained elevated in MPS II and all busulfan-conditioned mice. As we have previously shown, busulfan-conditioning leads to long-term increases in MCP-1 levels in the brain, a key mediator of cell transmigration to the CNS, and exerts a long-term trans-migratory effect. Approximately 20% of intravenously injected busulfan can cross the BBB, driving an even stronger pro-migratory MCP-1 response, which may ultimately facilitate the transmigration of donor-derived leukocytes across the BBB into the CNS in MPS II mice and provide additional means of trafficking enzyme into brain parenchyma.

Microglial activation and astrocytosis are commonly reported in MPS disorders, including this study. We observed a complete abrogation of GFAP and LAMP2 staining in the cortex, caudate putamen, hippocampus and amygdala of LV.IDS.ApoEII mice, with only partial correction of the same areas in the LV.IDS group. Furthermore, complete normalisation of activated microglia was observed in the cortex and striatum of LV.IDS.ApoEII-treated mice, with only a 50% reduction in LV.IDS. LV.IDS.ApoEII treatment is comparable to the correction of astrogliosis and microglial activation reported using direct AAV9-IDS injection into the CSF (15). Peripheral inflammation was detected in livers of MPS II mice, with stark elevations in the levels of MCP-1, MIP-1α and RANTES, and was abrogated by all transplants, indicating that peripheral IDS enzyme levels obtained with an allogeneic transplant can mediate a reduction in inflammation in the periphery.

As a sensitive and widely accepted paradigm of exploratory behavior and spatial working memory, the Y-maze accounts for potential physical impairments in MPS II mice, unlike the Barnes maze, which may be invalidated by differential physical performance. Full behavioural correction of cognitive deficits was observed in the LV.IDS.ApoEII group alongside normalisation of coordination and balance. We hypothesise that cognitive improvements likely stems from a combination of factors; a reduction in primary storage of HS alongside full abrogation of chronic neuroinflammation, astrogliosis and microglial activation, all of which were only observed in LV.IDS.ApoEII-treated animals. The rescue of coordination and balance can be attributed to either central or peripheral rescue, or a combination thereof. Most importantly, this further highlights that the addition of the ApoE tandem peptide is absolutely necessary to target IDS enzyme to the brain to provide a full correction of the neurocognitive aspect in MPS II mice.

The present inventors and others have reported progressive skeletal abnormalities in the MPS II mouse model, such as enlargement of craniofacial bone structures and femurs), correlating with the dysostosis multiplex seen in MPS II patients. As little enzyme is targeted to the cartilage or bone lesions, ERT using idursulfase showed limited benefits in joint pain, stiffness, or range of motion, although earlier treatments could provide benefits. In our study, the widths of zygomatic arches, humerus and femurs were significantly reduced in all transplanted animals, including WT-HSCT, suggesting that some level of enzyme can penetrate bone tissue if treated at an early time point when skeletal phenotype remains mild. This is partly comparable to liver-directed AAV2/8TBG-IDS gene therapy, where craniofacial abnormalities were also corrected. Importantly, it is likely that sustained availability of enzyme to the skeleton and joints from an early time point is required for clinical improvements.

Cardiac involvement in MPS II ranges from progressive valvular pathology, left ventricular hypertrophy, increased wall thickness to systemic hypertension, yielding a complex cardiac phenotype that remains difficult to treat (49). A plethora of factors can trigger the activation of transcription factors, co-regulators and microRNAs that will alter cardiac gene expression. HS GAGs also partly regulate Sonic Hedgehog (Shh), involved in heart ontogenesis and cardiac regeneration, which is downregulated alongside Ptch1, FoxM1 and Bmp4 in MPS II mice. Expression of Nppb and Myh7, two genes previously implicated with heart failure in MPS IIIB mice, was elevated up to 18-fold and 9-fold over WT levels respectively, suggesting a significant deregulation of cardiac genes and cardiac pathways in MPS II mice that is rescued with all transplants. Hence, sustained delivery of IDS enzyme in the periphery can benefit heart tissue and restore normal cardiac gene expression, if only partially. Overall, it has been shown for the first time that the expression of cardiac genes involved in heart failure can be modulated to WT levels by transplanting HSCs expressing either endogenous or supra-physiological levels of IDS enzyme, and that this may be a significant step in treating the cardiorespiratory phenotype in MPS II patients.

Immunologically foreign proteins and enzymes such as ERT can trigger the release of inhibitory antibodies that may decrease therapeutic efficacy, although molecular and cellular chimerism after HSCT can induce tolerance to donor-specific antigens. IgG antibodies against human recombinant IDS in plasma of LV.IDS and LV.IDS.ApoEII-treated mice were not detected, and no adverse symptoms identified that could be attributed to neutralising antibodies. Overall, this is a strong indication that hematopoietic stem cell gene therapy (HSCGT) can induce tolerance and that both enzymes produced are well tolerated by the immune system. Lastly, the addition of the ApoEII peptide residue does not generate increased immune sensitivity when compared to unmodified IDS.

Significantly, the addition of the apoE tandem repeat to human IDS allows for complete correction of the neuroinflammation, neurodegeneration and cognitive behaviour in the MPS II mouse model, likely by a combination of increased uptake and enzyme stabilisation mechanisms. Previous gene therapy approaches have highlighted the therapeutic potential of BBB-fusion enzymes with the receptor-binding domain of other Apo complexes such as ApoB and ApoE to correct brain pathology in disease models of LSDs and their promising clinical use for MPS disorders. This is the first study highlighting the combined use of HSCGT and the ApoEII-fusion enzyme to fully correct the neurological, skeletal, inflammatory and behavioural phenotypes in MPS II mice. The experiments show the suitability HSCGT using ApoEII-modified enzyme for the treatment of MPS II patients.

The forgoing embodiments are not intended to limit the scope of the protection afforded by the claims, but rather to describe examples of how the invention may be put into practice.

Sequence Listings

```
(coIDS DNA sequence)
                                                          SEQ ID No. 1
atgcctccac ctagaactgg aagaggcctg ctgtggctgg gcctggtgct gtctagtgtg    60
tgtgtggccc tgggcagcga gacacaggcc aacagcacaa ccgacgccct gaacgtgctg   120
ctgatcatcg tggacgacct gaggcctagc ctgggctgct acggcgataa gctcgtgcgg   180 agcccaaca tcgatcagct ggcctctcac agcctgctgt tccagaacgc attcgcacag   240
caggcagtgt gcgcccccag cagagtgtct ttcctgaccg gcagaaggcc cgacaccacc   300
cggctgtacg acttcaacag ctactggcgg gtgcacgccg gcaacttcag caccatcccc   360
cagtacttca aagaaaacgg ctacgtgacc atgagcgtgg gcaaggtgtt ccacccggc   420 atcagctcca accacaccga cgacagcccc tacagctggt ccttcccacc ctaccacccc   480
agcagcgaga agtacgagaa caccaagacc tgcagaggcc ccgacggcga gctgcatgcc   540
aatctgctgt gccccgtgga cgtgctggat gtgcctgagg gaaccctgcc cgacaagcag   600
tctaccgagc aggccattca gctgctggaa aagatgaaga ccagcgccag ccccttcttc   660
```

-continued

```
ctggccgtgg gctatcacaa gccccacatc cctttcagat accccaaaga gttccagaag    720
ctgtaccccc tggaaaacat caccctggcc cccgatcctg aggtgccaga tggactgcct    780
cccgtggcct acaaccctg gatggacatc cggcagcgcg aggatgtgca ggccctgaat     840
atcagcgtgc cctacggccc catccccgtg gatttccagc ggaagatccg gcagagctac    900
ttcgccagcg tgtcctacct ggacacccaa gtgggcagac tgctgagcgc cctggacgat    960
ctgcagctgg ccaactccac catcattgcc ttcaccagcg accacggctg ggccctggga    1020
gaacatggcg agtgggccaa gtacagcaac ttcgacgtgg ccacccacgt gcccctgatc    1080
ttctacgtgc aggcagaaac cgccagcctg cctgaggctg cgagaagct gttcccttac     1140
ctggacccct tcgacagcgc ctcccagctg atggaacctg gcagacagag catggacctg    1200
gtggaactgg tgtccctgtt ccccacactg gccggactgg ctggactgca ggtgccccct    1260
agatgtcccg tgcctagctt tcacgtggaa ctgtgcagag agggcaagaa cctgctgaag    1320
cacttccggt tccgggacct ggaagaagat ccctacctgc ccgcaaccc cagagagctg     1380
atcgcctaca gccagtaccc cagacccagc gacatccctc agtggaacag cgacaagccc    1440
agcctgaagg acatcaagat catgggctac agcatccgga ccatcgacta ccggtacacc    1500
gtgtgggtgg gattcaaccc cgacgagttc ctggccaatt tctccgacat ccacgccggg    1560
gagctgtact tcgtggacag cgatcccctg caggaccaca acatgtacaa cgacagccag    1620
ggcggcgacc tgttccagct gctgatgccc                                     1650
```

(Wild Type IDS DNA Sequence)

SEQ ID No. 2

```
atgccgccac cccggaccgg ccgaggcctt ctctggctgg gtctggttct gagctccgtc     60
tgcgtcgccc tcggatccga aacgcaggcc aactcgacca cagatgctct gaacgttctt    120
ctcatcatcg tggatgacct gcgccccctc ctgggctgtt atggggataa gctggtgagg    180
tccccaaaata ttgaccaact ggcatcccac agcctcctct tccagaatgc ctttgcgcag    240
caagcagtgt gcgccccgag ccgcgtttct ttcctcactg gcaggagacc tgacaccacc    300
cgcctgtacg acttcaactc ctactggagg gtgcacgctg aaacttctc caccatcccc    360
cagtacttca aggagaatgg ctatgtgacc atgtcggtgg aaaagtctt tcaccctggg    420
atatcttcta accataccga tgattctccg tatagctggt cttttccacc ttatcatcct    480
tcctctgaga agtatgaaaa cactaagaca tgtcgagggc cagatggaga actccatgcc    540
aacctgcttt gccctgtgga tgtgctggat gttcccgagg gcaccttgcc tgacaaacag    600
agcactgagc aagccataca gttgttggaa aagatgaaaa cgtcagccag tccttctctt    660
ctggccgttg gtatcataa gccacacatc cccttcagat accccaagga atttcagaag    720
ttgtatcccc tggagaacat caccctggcc cccgatcccg aggtccctga tggcctaccc    780
cctgtggcct acaaccctg gatggacatc aggcaacggg aagacgtcca agccttaaac    840
atcagtgtgc cgtatggtcc aattcctgtg actttcagc ggaaaatccg ccagagctac    900
tttgcctctg tgtcatattt ggatacacag gtcggccgcc tcttgagtgc tttggacgat    960
cttcagctgg ccaacagcac catcattgca tttacctcgg atcatgggtg ggctctaggt    1020
gaacatggag aatgggccaa atacagcaat tttgatgttg ctacccatgt tcccctgata    1080
ttctatgttc ctggaaggac ggcttcactt ccggaggcag cgagaagct tttcccttac    1140
ctcgacccctt ttgattccgc ctcacagttg atggagccag caggcaatc catggaccct    1200
gtggaacttg tgtctctttt tcccacgctg gctggacttg caggactgca ggttccacct    1260
cgctgccccg ttccttcatt tcacgttgag ctgtgcagag aaggcaagaa ccttctgaag    1320
```

-continued

```
catttcgat tccgtgactt ggaagaggat ccgtacctcc ctggtaatcc ccgtgaactg    1380
attgcctata gccagtatcc ccggccttca gacatccctc agtggaattc tgacaagccg    1440
agtttaaaag atataaagat catgggctat tccatacgca ccatagacta taggtatact    1500 gtgtggttg gcttcaatcc tgatgaattt ctagctaact tttctgacat ccatgcaggg     1560
gaactgtatt ttgtggattc tgacccattg caggatcaca atatgtataa tgattcccaa    1620
ggtggagatc ttttccagtt gttgatgcct                                     1650
```

(ApoE tandem repeat (ApoEII) DNA Sequence)

SEQ ID No. 3

```
ctgagaaagc tgcggaagcg gctgctgctg aggaagctga aaaaagact gctg    54
```

(Linker DNA Sequence)

SEQ ID No. 4

```
ctgggagggg gaggatctgg cggaggcgga agtggcggcg gaggatcagg gggcggaggc    60
tct                                                                  63
```

(coIDS Amino Acid Sequence)

SEQ ID No. 5

```
MPPPRTGRGL LWLGLVLSSV CVALGSETQA NSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSEKYENTKT CRGPDGELHA   180
NLLCPVDVLD VPEGTLPDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGRLLSALDD LQLANSTIIA FTSDHGWALG EHGEWAKYSN FDVATHVPLI   360
FYVPGRTASL PEAGEKLFPY LDPFDSASQL MEPGRQSMDL VELVSLFPTL AGLAGLQVPP   420
RCPVPSFHVE LCREGKNLLK HFRFRDLEED PYLPGNPREL IAYSQYPRPS DIPQWNSDKP   480
SLKDIKIMGY SIRTIDYRYT VWVGFNPDEF LANFSDIHAG ELYFVDSDPL QDHNMYNDSQ   540
GGDLFQLLMP                                                          550
```

(Wild Type IDS Amino Acid Sequence)

SEQ ID No. 6

```
MPPPRTGRGL LWLGLVLSSV CVALGSETQA NSTTDALNVL LIIVDDLRPS LGCYGDKLVR    60
SPNIDQLASH SLLFQNAFAQ QAVCAPSRVS FLTGRRPDTT RLYDFNSYWR VHAGNFSTIP   120
QYFKENGYVT MSVGKVFHPG ISSNHTDDSP YSWSFPPYHP SSEKYENTKT CRGPDGELHA   180
NLLCPVDVLD VPEGTLPDKQ STEQAIQLLE KMKTSASPFF LAVGYHKPHI PFRYPKEFQK   240
LYPLENITLA PDPEVPDGLP PVAYNPWMDI RQREDVQALN ISVPYGPIPV DFQRKIRQSY   300
FASVSYLDTQ VGRLLSALDD LQLANSTIIA FTSDHGWALG EHGEWAKYSN FDVATHVPLI   360
FYVPGRTASL PEAGEKLFPY LDPFDSASQL MEPGRQSMDL VELVSLFPTL AGLAGLQVPP   420
RCPVPSFHVE LCREGKNLLK HFRFRDLEED PYLPGNPREL IAYSQYPRPS DIPQWNSDKP   480
SLKDIKIMGY SIRTIDYRYT VWVGFNPDEF LANFSDIHAG ELYFVDSDPL QDHNMYNDSQ   540
GGDLFQLLMP                                                          550
```

(ApoE tandem repeat (ApoEII) Amino Acid Sequence)

SEQ ID No. 7

```
LRKLRKRLLL RKLRKRLL    18
```

(Linker Amino Acid Sequence)

SEQ ID No. 8

```
LGGGGSGGGG SGGGGSGGGG S    21
```

REFERENCES

1. Neufeld E F, Muenzer J. The Mucopolysaccharidoses. In: McGraw-Hill, editor. Lysosomal Disorders 2001. p. 3421-52.
2. Baehner F, Schmiedeskamp C, Krummenauer F, Miebach E, Bajbouj M, Whybra C, et al. Cumulative incidence rates of the mucopolysaccharidoses in Germany. Journal of inherited metabolic disease. 2005; 28(6):1011-7.
3. Poorthuis B J, Wevers R A, Kleijer W J, Groener J E, de Jong J G, van Weely S, et al. The frequency of lysosomal storage diseases in The Netherlands. Human genetics. 1999; 105(1-2):151-6. Epub 1999/09/10.
4. Wraith J E, Scarpa M, Beck M, Bodamer O A, De Meirleir L, Guffon N, et al. Mucopolysaccharidosis type II (Hunter syndrome): a clinical review and recommendations for treatment in the era of enzyme replacement therapy. European journal of pediatrics. 2008; 167(3):267-77. Epub 2007/11/27.
5. Cardone M, Polito V A, Pepe S, Mann L, D'Azzo A, Auricchio A, et al. Correction of Hunter syndrome in the MPSII mouse model by AAV2/8-mediated gene delivery. Human molecular genetics. 2006; 15(7):1225-36. Epub 2006/03/01.
6. Meikle P J, Hopwood J J, Clague A E, Carey W F. Prevalence of lysosomal storage disorders. Jama. 1999; 281(3):249-54. Epub 1999/01/26.
7. Holt J B, Poe M D, Escolar M L. Natural Progression of Neurological Disease in Mucopolysaccharidosis Type II. Pediatrics. 2011; 127(5):E1258-E65.
8. Eng C, Muenzer J, Wraith E, Beck M, Giugliani R, Harmatz P, et al. Clinical benefit of enzyme replacement therapy (ERT) in mucopolysaccharidosis II (MPS II, Hunter syndrome). Molecular genetics and metabolism. 2007; 92(4):S18-S.
9. Muenzer J, Wraith J E, Beck M, Giugliani R, Harmatz P, Eng C M, et al. A phase II/III clinical study of enzyme replacement therapy with idursulfase in mucopolysaccharidosis II (Hunter syndrome). Genetics in Medicine. 2006; 8(8):465-73.
10. Muenzer J, Beck M, Eng C M, Giugliani R, Harmatz P, Martin R, et al. Long-term, open-labeled extension study of idursulfase in the treatment of Hunter syndrome. Genetics in Medicine. 2011; 13(2):95-101.
11. Scarpa M, Almassy Z, Beck M, Bodamer O, Bruce I A, De Meirleir L, et al. Mucopolysaccharidosis type II: European recommendations for the diagnosis and multidisciplinary management of a rare disease. Orphanet journal of rare diseases. 2011; 6:72. Epub 2011/11/09.
12. Brooks D A, Kakavanos R, Hopwood J J. Significance of immune response to enzyme-replacement therapy for patients with a lysosomal storage disorder. Trends in molecular medicine. 2003; 9(10):450-3. Epub 2003/10/15.
13. Wakabayashi T, Shimada Y, Akiyama K, Higuchi T, Fukuda T, Kobayashi H, et al. Hematopoietic Stem Cell Gene Therapy Corrects Neuropathic Phenotype in Murine Model of Mucopolysaccharidosis Type II. Hum Gene Ther. 2015. Epub 2015/03/13.
14. Hinderer C, Katz N, Louboutin J P, Bell P, Yu H, Nayal M, et al. Delivery of an adeno-associated virus vector into CSF attenuates central nervous system disease in mucopolysaccharidosis type II mice. Hum Gene Ther. 2016. Epub 2016/08/12.
15. Motas S, Haurigot V, Garcia M, Marco S, Ribera A, Roca C, et al. CNS-directed gene therapy for the treatment of neurologic and somatic mucopolysaccharidosis type II (Hunter syndrome). JCI Insight. 2016; 1(9).
16. Aldenhoven M, Jones S A, Bonney D, Borrill R E, Coussons M, Mercer J, et al. Hematopoietic cell transplantation for mucopolysaccharidosis patients is safe and effective: results after implementation of international guidelines. Biology of blood and marrow transplantation: journal of the American Society for Blood and Marrow Transplantation. 2015; 21(6):1106-9. Epub 2015/02/25.
17. Aldenhoven M, Wynn R F, Orchard P J, O'Meara A, Veys P, Fischer A, et al. Long-term outcome of Hurler syndrome patients after hematopoietic cell transplantation: an international multicenter study. Blood. 2015; 125(13):2164-72. Epub 2015/01/28.
18. Boelens J J, Aldenhoven M, Purtill D, Ruggeri A, Defor T, Wynn R, et al. Outcomes of transplantation using various hematopoietic cell sources in children with Hurler syndrome after myeloablative conditioning. Blood. 2013; 121(19):3981-7. Epub 2013/03/16.
19. Guffon N, Bertrand Y, Forest I, Fouilhoux A, Froissart R. Bone marrow transplantation in children with Hunter syndrome: outcome after 7 to 17 years. The Journal of pediatrics. 2009; 154(5):733-7. Epub 2009/01/27.
20. Vellodi A, Young E, Cooper A, Lidchi V, Winchester B, Wraith J E. Long-term follow-up following bone marrow transplantation for Hunter disease. Journal of inherited metabolic disease. 1999; 22:638-48.
21. Visigalli I, Delai S, Politi L S, Di Domenico C, Cerri F, Mrak E, et al. Gene therapy augments the efficacy of hematopoietic cell transplantation and fully corrects mucopolysaccharidosis type I phenotype in the mouse model. Blood. 2010; 116(24):5130-9. Epub 2010/09/18.
22. Biffi A, Visigalli I. Hematopoietic Stem Cell Gene Therapy for Lysosomal Storage Disorders: Expected Benefits and Limitations. Stem Cells Biol Reg. 2013:127-38.
23. Biffi A, De Palma M, Quattrini A, Del Carro U, Amadio S, Visigalli I, et al. Correction of metachromatic leukodystrophy in the mouse model by transplantation of genetically modified hematopoietic stem cells. The Journal of clinical investigation. 2004; 113(8):1118-29. Epub 2004/04/16.
24. Langford-Smith A, Wilkinson F L, Langford-Smith K J, Holley R J, Sergijenko A, Howe S J, et al. Hematopoietic stem cell and gene therapy corrects primary neuropathology and behavior in mucopolysaccharidosis IIIA mice. Molecular therapy: the journal of the American Society of Gene Therapy. 2012; 20(8):1610-21. Epub 2012/05/02.
25. Sergijenko A, Langford-Smith A, Liao A Y, Pickford C E, McDermott J, Nowinski G, et al. Myeloid/Microglial driven autologous hematopoietic stem cell gene therapy corrects a neuronopathic lysosomal disease. Molecular therapy: the journal of the American Society of Gene Therapy. 2013; 21(10):1938-49. Epub 2013/06/12.
26. Pardridge W M. Molecular biology of the blood-brain barrier. Molecular biotechnology. 2005; 30(1):57-70. Epub 2005/04/05.
27. Pardridge W M. Targeting neurotherapeutic agents through the blood-brain barrier. Archives of neurology. 2002; 59(1):35-40. Epub 2002/01/16.
28. Boren J, Lee I, Zhu W, Arnold K, Taylor S, Innerarity T L. Identification of the low density lipoprotein receptor-binding site in apolipoprotein B100 and the modulation of its binding activity by the carboxyl terminus in familial defective apo-B100. The Journal of clinical investigation. 1998; 101(5):1084-93. Epub 1998/04/16.
29. Sorrentino N C, D'Orsi L, Sambri I, Nusco E, Monaco C, Spampanato C, et al. A highly secreted sulphamidase engineered to cross the blood-brain barrier corrects brain lesions of mice with mucopolysaccharidoses type IIIA. Embo Mol Med. 2013; 5(5):675-90. Epub 2013/04/10.
30. Spencer B, Verma I, Desplats P, Morvinski D, Rockenstein E, Adame A, et al. A neuroprotective brain-penetrating endopeptidase fusion protein ameliorates Alzheimer disease pathology and restores neurogenesis. The Journal of biological chemistry. 2014; 289(25):17917-31. Epub 2014/05/16.
31. Spencer B J, Verma I M. Targeted delivery of proteins across the blood-brain barrier. Proc Natl Acad Sci USA. 2007; 104(18):7594-9. Epub 2007/04/28.
32. Bockenhoff A, Cramer S, Wolte P, Knieling S, Wohlenberg C, Gieselmann V, et al. Comparison of five peptide vectors for improved brain delivery of the lysosomal enzyme arylsulfatase A. The Journal of neuroscience: the official journal of the Society for Neuroscience. 2014; 34(9):3122-9. Epub 2014/02/28.
33. Wang D, El-Amouri S S, Dai M, Kuan C Y, Hui D Y, Brady R O, et al. Engineering a lysosomal enzyme with a derivative of receptor-binding domain of apoE enables delivery across the blood-brain barrier. Proc Natl Acad Sci USA. 2013; 110(8):2999-3004. Epub 2013/02/06.
34. Bigger B W, Siapati E K, Mistry A, Waddington S N, Nivsarkar M S, Jacobs L, et al. Permanent partial phenotypic correction and tolerance in a mouse model of hemophilia B by stem cell gene delivery of human factor IX. Gene therapy. 2006; 13(2):117-26.
35. Siapati E K, Bigger B W, Miskin J, Chipchase D, Parsley K L, Mitrophanous K, et al. Comparison of HIV- and EIAV-based vectors on their efficiency in transducing murine and human hematopoietic repopulating cells. Molecular Therapy. 2005; 12(3):537-46.
36. Kuroda H, Kutner R H, Bazan N G, Reiser J. Simplified lentivirus vector production in protein-free media using polyethylenimine-mediated transfection. J Virol Methods. 2009; 157(2):113-21.
37. Lu J Z, Hui E K, Boado R J, Pardridge W M. Genetic engineering of a bifunctional IgG fusion protein with iduronate-2-sulfatase. Bioconjugate chemistry. 2010; 21(1):151-6. Epub 2009/12/17.
38. Holley R J, Deligny A, Wei W, Watson H A, Ninonuevo M R, Dagalv A, et al. Mucopolysaccharidosis Type I, Unique Structure of Accumulated Heparan Sulfate and Increased N-Sulfotransferase Activity in Mice Lacking alpha-L-iduronidase. Journal of Biological Chemistry. 2011; 286(43):37515-24.
39. Nolan T, Hands R E, Bustin S A. Quantification of mRNA using real-time R T-PCR. Nature protocols. 2006; 1(3):1559-82.
40. Wilkinson F L, Holley R J, Langford-Smith K J, Badrinath S, Liao A, Langford-Smith A, et al. Neuropathology in mouse models of mucopolysaccharidosis type I, IIIA and IIIB. PloS one. 2012; 7(4):e35787. Epub 2012/05/05.
41. Jiang L, O'Leary C, Kim H A, Parish C L, Massalas J, Waddington J L, et al. Motor and behavioral phenotype in conditional mutants with targeted ablation of cortical D1 dopamine receptor-expressing cells. Neurobiology of disease. 2015; 76:137-58. Epub 2015/02/17.
42. O'Tuathaigh C M P, Babovic D, O'Sullivan G J, Clifford J J, Tighe O, Croke D T, et al. Phenotypic characterization of spatial cognition and social behavior in mice with 'knockout' of the schizophrenia risk gene neuregulin 1. Neuroscience. 2007; 147(1):18-27.

The invention claimed is:

1. A nucleic acid comprising an iduronate-2-sulfatase (IDS) gene sequence and a tandem repeat of an Apolipoprotein E (ApoEII) gene sequence, further comprising an intervening linker sequence located between the IDS sequence and the ApoEII sequence, wherein the intervening linker sequence comprises the sequence according to SEQ ID No. 4 or a derivative sequence having at least 95% homology to SEQ ID No. 4.

2. The nucleic acid of claim 1, wherein the IDS sequence comprises a codon-optimised sequence of the wild-type IDS sequence.

3. The nucleic acid of claim 1, wherein the IDS sequence comprises the sequence according to SEQ ID No. 1 or SEQ ID No. 2 or a derivative sequence having at least 90% homology to SEQ ID No. 1 or SEQ ID No. 2, or the ApoEII sequence comprises one or more sequences according to SEQ ID No. 3 or a derivative sequence having at least 95% homology to SEQ ID No. 3.

4. The nucleic acid of claim 1, wherein the nucleic acid is incorporated in a gene therapy vector.

5. The nucleic acid of claim 4, wherein the vector is a lentiviral vector.

6. The nucleic acid of claim 1, wherein the nucleic acid is transduced in one or more haematopoietic stem and progenitor cells (HSPCs).

7. A combination of the nucleic acid of claim 1 and one or more haematopoietic stem and progenitor cells (HSPCs), wherein the nucleic acid is capable of transducing the HSPCs.

* * * * *